(12) United States Patent
Goodwin et al.

(10) Patent No.: US 11,890,194 B2
(45) Date of Patent: Feb. 6, 2024

(54) TRANSLATION CATHETERS, SYSTEMS, AND METHODS OF USE THEREOF

(71) Applicant: Edwards Lifesciences Corporation, Irvine, CA (US)

(72) Inventors: Jonathan Goodwin, Nashua, NH (US); Michael W. Sutherland, Pelham, NH (US); Morgan House, Newfields, NH (US); Richard J. Morrill, North Billerica, MA (US); Matt Guimond, Salem, NH (US); Christopher C. Lee, Tweksbury, MA (US); Kate E. Cutuli, Atkinson, NH (US); Nareak Douk, Lowell, MA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 691 days.

(21) Appl. No.: 16/886,682

(22) Filed: May 28, 2020

(65) Prior Publication Data
US 2020/0289266 A1    Sep. 17, 2020

Related U.S. Application Data

(60) Continuation of application No. 15/642,963, filed on Jul. 6, 2017, now Pat. No. 10,682,232, which is a
(Continued)

(51) Int. Cl.
*A61M 25/01* (2006.01)
*A61M 25/09* (2006.01)
*A61F 2/24* (2006.01)

(52) U.S. Cl.
CPC ....... *A61F 2/2466* (2013.01); *A61M 25/0133* (2013.01); *A61M 25/0147* (2013.01);
(Continued)

(58) Field of Classification Search
None
See application file for complete search history.

(56) References Cited

U.S. PATENT DOCUMENTS

| | | |
|---|---|---|
| 3,604,488 A | 9/1971 | Wishart et al. |
| 3,656,185 A | 4/1972 | Carpentier |

(Continued)

FOREIGN PATENT DOCUMENTS

| | | |
|---|---|---|
| CN | 13331995 A | 9/2021 |
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009:2;2;565-573 (2009).
(Continued)

*Primary Examiner* — Christine H Matthews
(74) *Attorney, Agent, or Firm* — Anya Adams

(57) ABSTRACT

A catheter system including a wire, a translatable catheter, and first and second tethers is introduced into a body of a subject. The translatable catheter has a curved portion proximate a distal end of the translatable catheter. The first tether is coupled to the wire, and passes proximally through the translatable catheter. The second tether is attached to the curved portion. The catheter system is positioned such that the wire is disposed at a first location in the body. While the wire remains at the first location, the translatable catheter is translated away from the wire by manipulating the first tether and the second tether. Other embodiments are also described.

24 Claims, 11 Drawing Sheets

Related U.S. Application Data division of application No. 14/210,967, filed on Mar. 14, 2014, now Pat. No. 9,724,195.

(60) Provisional application No. 61/786,373, filed on Mar. 15, 2013.

(52) U.S. Cl.
CPC . *A61M 25/09041* (2013.01); *A61M 2025/015* (2013.01); *A61M 2025/018* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |

(56) References Cited

U.S. PATENT DOCUMENTS

| | | |
|---|---|---|
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |

(56) References Cited

U.S. PATENT DOCUMENTS

| | | |
|---|---|---|
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |

(56) References Cited

U.S. PATENT DOCUMENTS

| | | |
|---|---|---|
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137700 A1 | 6/2005 | Spence et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299387 A1 | 12/2007 | Williams et al. |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |

(56) References Cited

U.S. PATENT DOCUMENTS

| | | |
|---|---|---|
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0182268 A1* | 7/2009 | Thielen ............ A61M 25/0138 604/95.04 |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0103055 A1 | 4/2013 | Schaller et al. |
| 2013/0116776 A1 | 5/2013 | Gross et al. |
| 2013/0123910 A1 | 5/2013 | Cartledge et al. |

(56) References Cited

U.S. PATENT DOCUMENTS

| | | |
|---|---|---|
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0000464 A1 | 1/2022 | Schaller et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | 2012111761 A1 | 8/2012 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |

(56) References Cited

FOREIGN PATENT DOCUMENTS

| WO | 2022224071 A1 | 10/2022 |
|---|---|---|
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.
Ahmadi, All et al. "Percutaneously adjustable pulmonary artery band." The Annals of thoracic surgery 60 (1995): S520-S522.
Alfieri et al."Novel Suture Device for Beating-Heart Mitral Leaflet Approximation", Ann Thorac Surg. 2002, 74:1488-1493.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri et al., "The edge to edge technique," The European Association for Cardio-Thoracic Surgery 14th Annual Meeting Oct. 7-11, Book of Procees. (2000).
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
Amplatzer® Cribriform Occluder. A patient guide to Percutaneous, Transcatheter, Atrial Septal Defect Closuer, AGA Medical Corporation, Apr. 2008.
Amplatzer® Septal Occluder. A patient guide to the Non-Surgical Closuer of the Atrial Septal Defect Using the Amplatzer Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. Ring+String, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio- thoracic Surgery 17 (2000) 201-205.
O'Reilly S et al., "Heart valve surgery pushes the envelope," Medtech Insight 8(3): 73, 99-108 (2006).
Odell JA et al., "Early Results o4yf a Simplified Method of Mitral Valve Annuloplasty," Circulation 92:150-154 (1995).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

TRANSLATION CATHETERS, SYSTEMS, AND METHODS OF USE THEREOF

CROSS REFERENCE TO RELATED APPLICATION

The present application is a Continuation of U.S. patent application Ser. No. 15/642,963, filed Jul. 6, 2017, which is a divisional of U.S. patent application Ser. No. 14/210,967, filed Mar. 14, 2014 (now U.S. Pat. No. 9,724,195), which claims the benefit of U.S. provisional patent application 61/786,373, filed Mar. 15, 2013, each of which is incorporated herein by reference in their entirety for all purposes.

TECHNICAL FIELD

The present invention relates generally to a delivery catheter system that is adapted to deliver multiple devices, such as guide wires, with definite spacing between each of them. The present invention further relates to a translation mechanism of the delivery catheter system which allows a delivery catheter to move to a definite distance.

BACKGROUND

The left side of a human heart includes the left atrium (LA) and the left ventricle (LV). An aorta receives oxygenated blood from the left ventricle through an aortic valve, which serves to prevent regurgitation of blood back into the left ventricle. A mitral valve is positioned between the left atrium and the left ventricle and allows one-way flow of the oxygenated blood from the left atrium to the left ventricle.

Mitral valve, which will be described below in more detail, includes an anterior leaflet and a posterior leaflet that are coupled to chordae tendineae. Chordae tendineae serve as "tension members" that prevent the leaflets of the mitral valve from moving past their closing point and prolapsing back into the left atrium. When the left ventricle contracts during systole, chordae tendineae limit the upward motion (toward the left atrium) of the anterior and posterior leaflets past the point at which the anterior and posterior leaflets meet and seal to prevent backflow from the left ventricle to the left atrium ("mitral regurgitation" or "mitral insufficiency"). Chordae tendineae arise from a columnae carnae or, more specifically, a musculi papillares (papillary muscles) of the columnae carnae. In various figures herein, some anatomical features have been deleted solely for clarity.

The anterior leaflet and the posterior leaflet of the mitral valve are generally thin, flexible membranes. When the mitral valve is closed, the anterior leaflet and the posterior leaflet are generally aligned and contact one another along a "line of coaptation" several millimeters back from their free edges, to create a seal that prevents mitral regurgitation. Alternatively, when the mitral valve is opened, blood flows downwardly through an opening created between the anterior leaflet and the posterior leaflet into left ventricle.

Many problems relating to the mitral valve may occur and may cause many types of ailments. Such problems include, but are not limited to, mitral regurgitation. Mitral regurgitation, or leakage, is the backflow of blood from the left ventricle into the left atrium due to an imperfect closure of the mitral valve. That is, leakage often occurs when the anterior and posterior leaflets do not seal against each other, resulting in a gap between the anterior leaflet and the posterior leaflet when the leaflets are supposed to be fully coapted during systole.

In general, a relatively significant systolic gap may exist between the anterior leaflet and the posterior leaflet for a variety of different reasons. For example, a gap may exist due to congenital malformations, because of ischemic disease, or because the heart has been damaged by a previous heart attack. Such a gap may also be created when congestive heart failure, e.g., cardiomyopathy, or some other type of distress which causes a heart to be enlarged. Enlargement of the heart can result in dilation (stretching) of the mitral annulus. This enlargement is usually limited to the posterior valve annulus and is associated with the posterior leaflet, because the anterior annulus is a relatively rigid fibrous structure. When the posterior annulus enlarges, it causes the posterior leaflet to move away from the anterior leaflet, causing a gap during systole because the two leaflets no longer form proper coaptation. This results in leakage of blood through the valve or regurgitation.

Blood leakage through the mitral valve generally causes a heart to operate less efficiently, as the heart pumps blood both out to the body via the aorta, and also back (in the form of mitral regurgitation) into the left atrium. Leakage through the mitral valve, or general mitral insufficiency, is thus often considered to be a precursor to congestive heart failure (CHF) or a cause of progressive worsening of heart failure. There are generally different levels of symptoms associated with heart failure. These levels are classified by the New York Heart Association (NYHA) functional classification system. The levels range from a Class 1 level which is associated with an asymptomatic patient who has substantially no physical limitations to a Class 4 level which is associated with a patient who is unable to carry out any physical activity without discomfort and has symptoms of cardiac insufficiency even at rest. In general, correcting or reducing the degree of mitral valve leakage may be successful in allowing the NYHA classification grade of a patient to be reduced. For instance, a patient with a Class 4 classification may have his classification reduced to Class 3 or Class 2 and, hence, be relatively comfortable at rest or even during mild physical exertion. By eliminating the flow of blood backwards into the left atrium, therapies that reduce mitral insufficiency reduce the workload of the heart and may prevent or slow the degradation of heart function and congestive heart failure symptoms that is common when a significant degree of mitral insufficiency remains uncorrected.

Treatments used to correct for mitral valve leakage or, more generally, CHF, are typically highly invasive, open-heart surgical procedures. In extreme cases, this may include implantation of a ventricular assist device such as an artificial heart in a patient with a failing heart. The implantation of a ventricular assist device is often expensive, and a patient with a ventricular assist device must be placed on extended anti-coagulant therapy. Anti-coagulant therapy reduces the risk of blood clot formation for example, within the ventricular assist device. Reducing the risks of blood clots associated with the ventricular assist device is desirable, but anti-coagulant therapies may increase the risk of uncontrollable bleeding in a patient, e.g., as a result of a fall.

Rather than implanting a ventricular assist device, bi-ventricular pacing devices similar to pacemakers may be implanted in some cases, e.g., cases in which a heart beats inefficiently in a particular asynchronous manner. While the implantation of a bi-ventricular pacing device may be effective, not all heart patients are suitable for receiving a bi-ventricular pacing device. Further, the implantation of a bi-ventricular pacing device is expensive, and is generally not effective in significantly reducing or eliminating the degree of mitral regurgitation.

Open-heart surgical procedures that are intended to correct for mitral valve leakage, specifically, can involve the implantation of a replacement valve. Valves from animals, e.g., pigs, may be used to replace a mitral valve in a human. While a pig valve as a replacement for the mitral valve may be relatively successful, such replacement valves generally wear out, thereby requiring additional open surgery at a later date. Mechanical valves, which are less likely to wear out, may also be used to replace a leaking mitral valve. However, when a mechanical valve is implanted, there is an increased risk of thromboembolism, and a patient is generally required to undergo extended anti-coagulant therapies.

A less invasive surgical procedure involves heart bypass surgery associated with a port access procedure. For a port access procedure, the heart may be accessed by cutting between ribs or sometimes removing parts of one or more ribs, as opposed to dividing the sternum to open the entire chest of a patient.

One open-heart surgical procedure that is particularly successful in correcting a mitral valve leakage and, in addition, mitral regurgitation, is an annuloplasty procedure. During an annuloplasty procedure, a medical device such as an annuloplasty ring may be implanted surgically on the left atrial side of mitral annulus (i.e., generally the attachment location of the base of the mitral valve to the heart). The device reduces a dilated mitral valve annulus to a relatively normal size and, specifically, moves the posterior leaflet closer to the anterior leaflet to aid anterior-posterior leaflet coaptation and thus improve the quality of mitral valve closure during systole. Annuloplasty rings are often shaped substantially like the letter "D" to correspond to the natural shape of the mitral annulus as viewed from above. Typically, the rings are formed from a rod or tube of biocompatible material, e.g., plastic, that has a DACRON mesh covering.

In order for an annuloplasty ring to be implanted, a surgeon surgically attaches the annuloplasty ring to the mitral valve on the atrial side of the mitral valve. Conventional methods for installing a ring require open-heart surgery which involves opening a patient's sternum and placing the patient on a heart bypass machine. The annuloplasty ring is sewn on a top portion of the mitral valve. In sewing the annuloplasty ring onto the mitral valve, a surgeon generally sews the straight side of the "D" to the fibrous tissue located at the junction between the posterior wall of the aorta and the base of the anterior mitral valve leaflet. As the curved part of the ring is sewn to the posterior aspect of the annulus, the surgeon alternately acquires a relatively larger amount of tissue from the mitral annulus, e.g., a one-eighth inch bite of tissue, using a needle and thread, compared to a relatively smaller bite taken of the fabric covering of the annuloplasty ring. Once the thread has loosely coupled the annuloplasty ring to the mitral valve annulus tissue, the annuloplasty ring is slid into contact with the mitral annulus. The tissue of the posterior mitral annulus that was previously stretched out, e.g., due to an enlarged heart, is effectively reduced in circumference and pulled forwards towards the anterior mitral leaflet by the tension applied by annuloplasty ring with the suture or thread. As a result, a gap between the anterior leaflet and the posterior leaflet during ventricular contraction or systole may be reduced and even substantially closed off in many cases thereby significantly reducing or even eliminating mitral insufficiency. After the mitral valve is shaped by the ring, the anterior and posterior leaflets will reform typically by pulling the posterior leaflet forward to properly meet the anterior leaflet and create a new contact line that will enable the mitral valve to appear and to function properly.

Although a patient that receives an annuloplasty ring may be subjected to anti-coagulant therapies, therapies are not extensive, as a patient is only subjected to therapies for a matter of weeks, e.g., until tissue grows over the annuloplasty ring.

Another type of procedure that is generally effective in reducing mitral valve leakage associated with prolapse of the valve leaflets involves placing a single edge-to-edge suture in the mitral valve that opposes the mid-portions of anterior and posterior leaflets. For example, in an Alfieri stitch or a bow-tie repair procedure, an edge-to-edge stitch is made at approximately the center of the gap between an anterior leaflet and a posterior leaflet of a mitral valve. Once the stitch is in place between the anterior and posterior leaflets, it is pulled in to form a suture which holds the anterior leaflet against the posterior leaflet.

Another surgical procedure that reduces mitral valve leakage involves placing sutures along a mitral valve annulus around the posterior leaflet. These sutures may be formed as a double track, e.g., in two "rows" from a single strand of suture material. The sutures are tied off at approximately a central point of posterior leaflet. Pledgets are often positioned under selected sutures to prevent the sutures from tearing through annulus. When the sutures are tightened and tied off, the circumference of the annulus may effectively be reduced to a desired size such that the size of a systolic gap between posterior leaflet and an anterior leaflet may be reduced.

While invasive surgical procedures have proven to be effective in the treatment of mitral valve leakage, invasive surgical procedures often have significant drawbacks. Any time a patient undergoes open-heart surgery, there is a risk of infection. Opening the sternum and using a cardiopulmonary bypass machine has also been shown to result in a significant incidence of both short and long term neurological deficits. Further, given the complexity of open-heart surgery, and the significant associated recovery time, people that are not greatly inconvenienced by CHF symptoms, e.g., people at a Class 1 classification, may choose not to have corrective surgery. In addition, people that need open heart surgery the most, e.g., people at a Class 4 classification, may either be too frail or too weak to undergo the surgery. Hence, many people that may benefit from a surgically repaired mitral valve may not undergo surgery.

In another method, a cinching device is placed within the coronary sinus (CS) using a catheter system, with distal, mid, and proximal anchors within the lumen of the CS to allow plication of the annulus via the CS. In practice, these anchors are cinched together and the distance between them is shortened by pulling a flexible tensile member such as a cable or suture with the intent being to shorten the valve annulus and pull the posterior leaflet closer to the anterior leaflet in a manner similar to an annuloplasty procedure. Unfortunately, since the tissue that forms the CS is relatively delicate, the anchors are prone to tear the tissue during the cinching procedure. In addition, the effect on the mitral annulus may be reduced when the CS of a particular patient is not directly aligned with the mitral annulus. Other minimally invasive techniques have been proposed but have various drawbacks related to such factors as effectiveness and/or accuracy of catheter-based implementation.

Catheter-based surgical procedures have been used to repair a defective mitral valve. Specifically, anchors are secured at a plurality of locations distributed around the annulus near the posterior leaflet of a mitral valve. Each anchor has a suture coupled thereto. The sutures are collectively gathered and pulled tight. As the sutures are pulled, the tissue between each pair of adjacent anchors is plicated, thereby shortening the length of the annulus and drawing the posterior leaflet toward the anterior leaflet. Similar techniques can also be used to repair a defective tricuspid valve.

During a surgical procedure, anchors are usually introduced and secured sequentially. A typical repair by using the catheter based surgical procedure involves a sequence that includes introducing a catheter to a proximity of the annulus, making an incision at the annulus, introducing a guide wire through the incision site, withdrawing the catheter, introducing an anchor by tracking a second catheter through the guide wire, securing the anchor in the annulus, and withdrawing the second catheter. This sequence is repeated to secure a second anchor.

Catheters capable of delivering multiple guide wires or anchors have been disclosed. Without claiming to have exhaustively examined prior art references and without attempting to characterizing any prior art reference, U.S. Patent Application Publication No. 2008-0228265 discloses a triple lumen catheter. However, distances between two of the three lumens are usually fixed. In addition, during a deployment, the two outer catheters are generally advanced lengthwise as well as laterally. In certain instances, one or both of the two outer catheters are caught by chordae tendineae during the deployment.

There is generally a need for an improved catheter to simplify the catheter-based mitral valve correction.

SUMMARY

One aspect of the present teachings generally relates to translation catheter systems. The catheter system comprises a first wire configured to be positioned at a first location, a second catheter configured to be positioned at a second location, and a translation element configured to move the second catheter from the first location to the second location in a substantially linear fashion. A first wire is positioned with the first catheter. The translation element operably connects the first and second catheters.

In one aspect of the present teachings, the translation element of the catheter system is a tether. The tether comprises a free end and the free end wraps around one of the first and second catheter. In one aspect of the present teachings, the tether comprises a fixed end and the fixed end. The fixed end is connected with one of the first and second catheter, and the free end extends into a lumen of the other catheter.

In another aspect of the present teachings, the translation element of the catheter system is a bar formed of at least two segments. In another aspect of the present teachings, the translation element of the catheter system comprises an anchor configured to track over the first wire, and a tether. The tether has a proximal end and a distal end, wherein the distal end of the tether connects the anchor.

In one aspect of the present teachings, the distal portions of the first and the second catheters are connected. In one aspect of the present teachings, the second catheter is flexible. In one aspect of the present teachings, the second catheter comprises at least one side opening. In one aspect of the present teachings, the distance between the first location and the second location is adjustable.

Another aspect of the present teachings generally relates to translation catheter systems where translation catheter systems have a first catheter configured to be positioned at a first treatment location; a second catheter configured to be positioned at a second treatment location; and a translation mechanism operably connecting the first and second catheters. In one aspect of the present teachings, the translation mechanism is configured to allow the second catheter to move laterally away from the first catheter to any distance.

Another aspect of the present teachings generally relates to translation catheter systems where translation catheter systems have a first guide wire positioned at a first treatment location; a tracking anchor configured to track over the first guide wire; a second catheter configured to be positioned at a second treatment location; and a tether having a proximal end and a distal end. The distal end of the tether connects to the tracking anchor and the proximal end of the tether extends through a central lumen of the second catheter.

Another aspect of the present teachings generally relates to translation catheter systems where translation catheter systems have a first catheter configured to be positioned at a first treatment location; a second catheter configured to be positioned at a second treatment location; and a tether having a proximal end and a distal end. The distal end of the tether connects to the first catheter and the proximal end of the tether extends through a central lumen of the second catheter.

Another aspect of the present teachings generally relates to translation catheter systems where translation catheter systems have a first catheter comprising a distal end configured to be positioned at a first treatment location; a second catheter comprising a distal end configured to be positioned at a second treatment location; and a connecting bar connecting the distal ends of the first and second catheters. The connecting bar has at least two segments with at least one pivot between the segments.

Another aspect of the present teachings generally relates to translation catheter systems where translation catheter systems have a first catheter comprising a distal end configured to be positioned at a first treatment location; and a second catheter comprising a distal end configured to be positioned at a second treatment location. The second catheter is configured to be bendable in one direction and the distal ends of the first and second catheters are joined to each other.

DETAILED DESCRIPTION OF CERTAIN EMBODIMENTS

Figure 1:
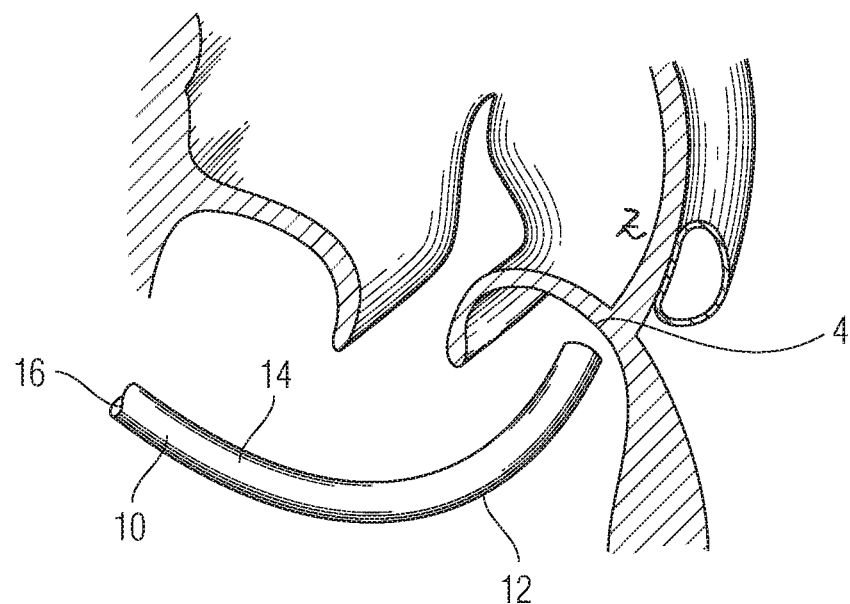
FIG. 1 is a perspective view of an exemplary wire delivery catheter in accordance with the present teachings.

Certain specific details are set forth in the following description and Figures to provide an understanding of various embodiments of the present teachings. Those of ordinary skill in the relevant art will understand that they can practice other embodiments of the present teachings without one or more of the details described herein. Thus, it is not the intention of the Applicants to restrict or in any way limit the scope of the appended claims to such details. While various processes are described with reference to steps and sequences in the following disclosure, the steps and sequences of steps should not be taken as required to practice all embodiments of the present teachings.

As used herein, the terms "subject" and "patient" refer to an animal, such as a mammal, such as livestock, pets, and preferably a human. Specific examples of "subjects" and "patients" include, but are not limited to, individuals requiring medical assistance and, in particular, requiring treatment for symptoms of a heart failure.

As used herein, the term "lumen" means a canal, duct, generally tubular space or cavity in the body of a subject, including veins, arteries, blood vessels, capillaries, intestines, and the like. The term "lumen" can also refer to a tubular space in a catheter, a sheath, or the like in a device.

As used herein, the term "proximal" means close to the operator (less into the body) and "distal" shall mean away from the operator (further into the body). In positioning a medical device from a downstream access point, distal is more upstream and proximal is more downstream.

While the description above refers to and the term "tether" means a tensioning member which can take forms of a suture, a wire, a strand, a cord, a fiber, a yarn, a filament, a cable, a thread, or the like. Thus, all these terms are essentially interchangeable and further include embodiments in which the wire, string, suture or filament is a hollow tube or conduit to allow another wire, as needed, to pass through its longitudinal axis. Each tether, wire, string, suture and filament can comprise one or more tethers, wires, strings, sutures and filaments. Material used to make tether could be flexible, semi-rigid, or rigid material having a suitably high tensile strength for the intended use.

As used herein, the term "catheter" or "sheath" encompasses any hollow instrument capable of penetrating body tissue or interstitial cavities and providing a conduit for selectively injecting a solution or gas. The term "catheter" or "sheath" is also intended to encompass any elongate body capable of serving as a conduit for one or more of the ablation, expandable or sensing elements. Specifically, in the context of coaxial instruments, the term "catheter" or "sheath" can encompass either the outer catheter body or sheath or other instruments that can be introduced through such a sheath. The use of the term "catheter" should not be construed as meaning only a single instrument but rather is used to encompass both singular and plural instruments, including coaxial, nested, and other tandem arrangements. Moreover, the terms "sheath" or "catheter" are sometime used interchangeably to describe catheters having at least one lumen through which instruments or treatment modalities can pass.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

An aspect of the present teachings provides a delivery catheter system for delivering multiple guide wires across mitral annulus at a controlled spacing between each of them. In various embodiments, the delivery catheter system has one catheter and a translation mechanism allowing the catheter to move to a second location, i.e. translate, from its first location by a distance, pre-defined or determined by a clinician during procedure. In some embodiments, the delivery catheter system includes two catheters and a translation mechanism allowing the at least one catheter to move away from the other catheter by a distance, pre-defined or determined by a clinician during procedure. In some embodiment, the distance between the first and second locations, or the distance between the first and second catheter after translation, are within the range of 1-40 mm. In some embodiment, the translation mechanism of the delivery catheter system includes a tether, a shuttle, a tracking element, a wire, a coil, a connecting bar with a pivot, or a combination thereof. In some embodiments, the translation is lateral. In other embodiments, the translation is distal-lateral. In some embodiments, the translation is continuous. In other embodiments, the translation is step-by-step. In some embodiments, the distance of the translation is adjustable. In other embodiments, the distance of the translation is pre-defined.

Another aspect of the present teachings provides method of delivering a translation catheter system to a first location at or approximate to the mitral annulus, translating the translation catheter system to a second location at or approximate to the mitral annulus. In various embodiments, the distance between the two locations is controlled by a clinician. In various embodiments, the method includes advancing a first delivery catheter to a first location at or approximate to the mitral annulus, placing a wire across the mitral annulus at this first location, translating the first catheter to a second location at or approximate to the mitral annulus, placing a second wire across the mitral annulus at the second location. In various embodiments, the method includes advancing a first delivery catheter to a first location at or approximate to the mitral annulus, placing a wire across the mitral annulus at this first location, translating the second catheter to a second location at or approximate to the mitral annulus, placing a second wire across the mitral annulus at the second location.

The following description refers to FIGS. 1 to 9. A person with ordinary skill in the art would understand that the figures and description thereto refer to various embodiments of the present teachings and, unless indicated otherwise by their contexts, do not limit the scope of the attached claims.

FIG. 1 illustrate a guide wire being delivered across a mitral annulus. According to one embodiment of the present teachings, a delivery sheath (not shown) is directed into the aorta, through the aortic valve, and into the left ventricle and between the chordae tendonae. The delivery sheath (not shown) is used as a conduit to deliver a first wire delivery catheter (10) to a treatment site. One ordinarily skilled in the art would understand that the first wire delivery catheter (10) can be advanced to a treatment location without a delivery sheath.

FIG. 1 illustrates an exemplary delivery of a first wire delivery catheter (10) according to the present teachings to a selected location adjacent to or near the mitral annulus (2). In some embodiments, the first catheter (10) advances through the longitudinal lumen of the delivery sheath (not shown) and is placed below the mitral annulus (2). In certain embodiments, the first catheter (10) has a proximal portion (not shown) remaining outside of the body, a distal end (12), an elongated body (14) between the proximal portion and the distal portion, and a central lumen (16) within the elongated body. In some embodiments, the distal end of the first catheter (10) can be turned, rotated, or deflected. The deflectability or steerability of the first catheter (10) allows a clinician to manipulate the distal end (12) of the first catheter (10) from outside of the body and advance it to a first location (4) near the annulus (2). Design and construction of a steerable and deflectable catheter are well known to those with ordinary skill in the art.

In some embodiments, the distal end (12) of the first catheter (10) includes a radio-opaque and/or echogenic marker so that the device can be visualized by using a radiographic imaging equipment, for example, x-ray, magnetic resonance, ultrasound, or fluoroscopic techniques.

Figure 2:
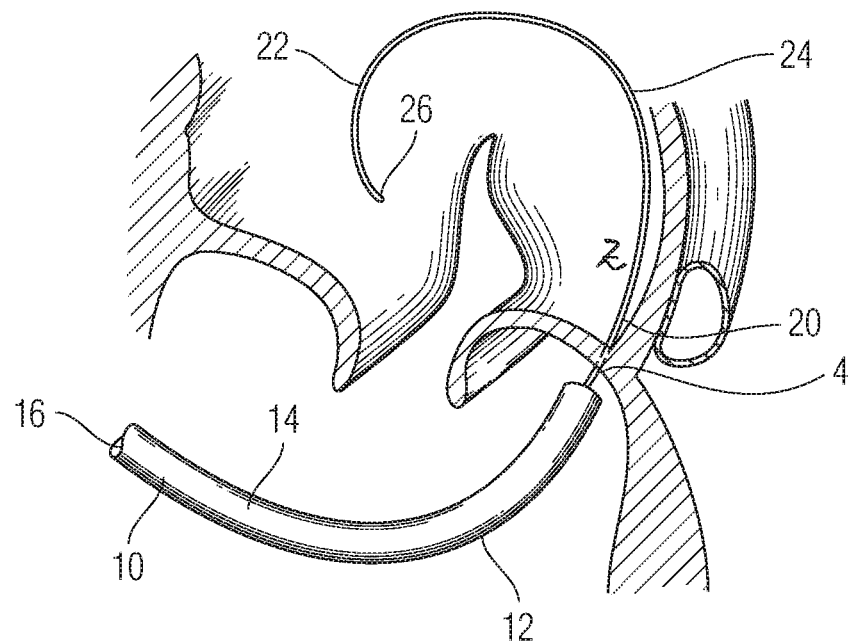
FIG. 2 is a perspective view of an exemplary wire deploying across a tissue in accordance with the present teachings.

FIG. 2 illustrates an example of the present teachings where a first wire (20) extends from a lumen (16) of a first catheter (10) and pierces the annulus (2). In various embodiments, the first wire (20) also includes a proximal end (not shown), a distal end (22), and an elongated body (24). In some embodiments, the first wire (20) is configured to slide within the lumen (16) of the first catheter (10). In some embodiments, the first wire (20) is configured to rotate within the lumen (16).

In various embodiments, the first wire (20) has a delivery profile where the distal end (22) of the first wire (20) is disposed inside the lumen (16) of the first catheter (10). In some embodiments, when the distal end (22) of the first wire (20) is disposed within the lumen (16) of the catheter (12), the entire first wire (20) is substantially straight and parallel with the long axis of the first catheter (10). In some embodiments, the first wire (20) has a deployed profiled where the distal end (22) of the first wire (20) extends distally outside the lumen (16) of the first catheter (10), as illustrated in FIG. 2. In certain embodiments, as the distal portion of the first wire (20) extends outside of the first catheter (10), the distal portion (22) transitions to a curved profile. Without intending to limit the scope of the present teachings, such a curved profile can prevent the first wire from causing unnecessary tissue damage inside the left atrium.

In various embodiments, the first wire (20) is pre-loaded within the lumen (16) of the first catheter (10). In various other embodiments, the first wire (20) is advanced after the first catheter (10) is placed at a treatment location.

In various embodiments, the first wire delivery catheter (10) is generally perpendicular to the annulus (2) before the first wire (20) pierces and crosses the annulus (2). Once the first catheter (10) is properly positioned, a clinician extends the first wire (20) distally so that the distal tip (26) of the first wire (20) pierces and crosses the annulus (2) at the first location (4). In some embodiments, a radio frequency energy is applied to assist the distal tip (26) of the first tissue piercing wire (20) to pierce and cross the annulus (2) and reach the left atrium. To determine when to stop the distal extension force to the wire (20), in some embodiments, a change of the counter force on the first wire (20) indicates that the annulus (2) is pierced or the distal tip (26) of the first wire (20) reaches a side wall of the left atrium. Alternatively, visualization techniques, including three-dimensional echocardiogram, fluoroscopy, or magnetic resonance imaging techniques, can be used.

Figure 3A:
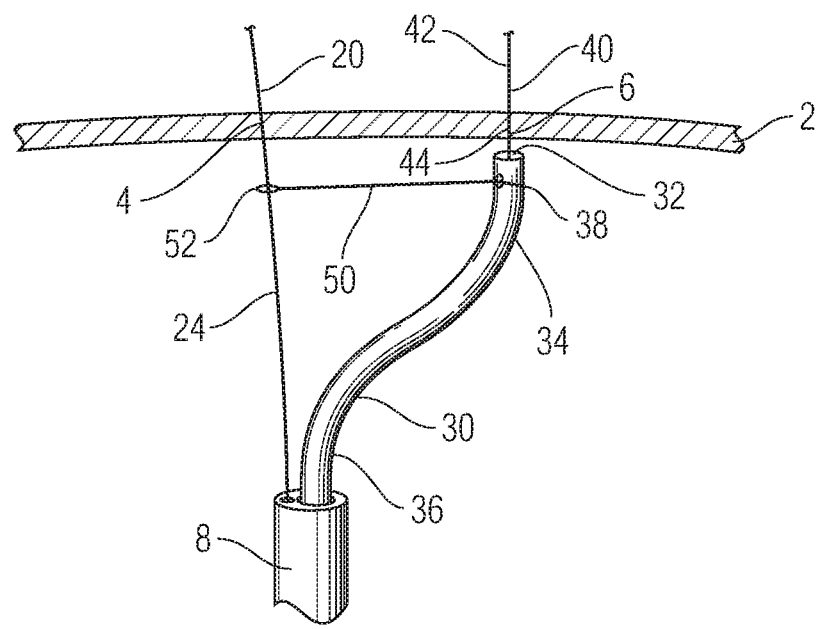
FIGS. 3A-D are perspective views of a translation catheter system in accordance with the present teachings.

FIGS. 3A-3D illustrate various embodiments of the translatable catheter system according to the present teachings. FIG. 3A illustrates an embodiment of the present teachings where a second wire (40) pierce the annulus (2). In various embodiments, when the first wire (20) is placed across the annulus (2), the first catheter (10) is retracted proximally and removed, a tracking element (52) is slid over the first wire (20) from its proximal end. In some embodiments, the tracking element (52) has the form of a loop, shuttle, or another shape (for example, including a lumen) so that the tracking element (52) can slide along the first wire (20) freely or in a controlled manner from the proximal end to the distal end (22, in FIG. 2) or from the distal end (22, in FIG. 2) to the proximal end (not shown).

As illustrated in FIG. 3A, the tracking element (52) is tethered to a second wire delivery catheter (30). Similar to the first wire delivery catheter (10), the second wire delivery catheter (30) includes a proximal portion (remaining outside of the body, not shown), a distal end (34) at or near the annulus (2), an elongated body (36) between the proximal end and the distal end, and a central lumen (32) extending throughout the elongated body (36). Similarly, a clinician can manipulate the second wire delivery catheter (30) to a second location near the annulus (2).

Further referring to FIG. 3A, a second wire (40) extends from the lumen (32) of the second catheter (30) and across the annulus (2). In various embodiments, the second wire (40) includes a proximal end (not shown), a distal end (42), and an elongated body (44). One ordinarily skilled in the art would understand that the first and second wires can have the same shape, size, and/or construct or different shapes, sizes, and/or constructs. Thus, what has been described herein should not be construed as limiting to the scope of the present teachings.

In an exemplary embodiment as shown in FIG. 3A, the second catheter (30) includes a side opening (38). The tether (50) extends from the tracking element (52), enters the side opening (38), extends proximally inside the lumen (32) of the second catheter (30), and exits outside of the body. In various embodiments, a clinician controls the proximal end of the tether. For example, a clinician can tighten the tether (50), for example, by pulling the tether (50) proximally, so that the distal end (34) of the second catheter (30) is pulled adjacent to the first wire (20). Or, for example, a clinician can loosen the tether (50), for example, by extending the tether (50) distally, so that the distal end (34) of the second catheter (30) is away from the first wire (20), as illustrated in FIG. 3A. The length of the tether (50) controls the distance between the distal end (34) of the second catheter (30) and the first wire (20).

To deliver the second wire (40) across the annulus (2), a clinician slides the tracking element (52) over the proximal end of the first wire (20) and affixes the tether (50) to the tracking element. The tether (50) and the tracking element (52) are loaded inside the second wire delivery catheter (30). By tightening the tether (50), the distal end (34) of the second catheter (30) maintains a close proximity to the first wire (20). The tracking element (52) and the second catheter (30), optionally disposed inside a delivery sheath (8), tracks along the first wire (20) and extends distally. Once the distal end (34) of the second catheter (30) arrives at or near to the first location (4) of the annulus (2), the tether (50) is loosened and the second catheter (30) is steered away from the first location (4) of the annulus (2) to the second location (6) on the annulus (2). In some embodiments, the translation of the second catheter (30) from the first location (4) is lateral. In other embodiments, the translation of the second catheter (30) from the first location (4) is continuous. In yet another embodiment, the translation distance of the second catheter (30) from the first location is adjustable.

In various embodiments, the second wire delivery catheter (30) is generally perpendicular to the annulus (2) before the second wire (40) pierces the annulus (2). The second wire (40) is advanced distally to pierce and cross the annulus (2) at the second location (6) in a manner similar to those described herein in connection with FIG. 2.

In some embodiments, the distal end (34) of the second catheter (30) remains close to the annulus (2) the entire time when the second catheter is steered from the first location to the second location. Without intending to limit the scope of the present teachings, such a lateral movement avoids the distal end of the second catheter from being caught, snag, or hung up by tissues in the left ventricle, and allows the second catheter (30) pushing away any anatomy in the path of the translation. In some embodiments, the distal end (34) of the second catheter (30) remains close to the annulus (2) the entire time when it is steered from the first location to the second location.

In one embodiment, a clinician controls the distance between the first and second locations (4, 6) by controlling the length of the tether (50) between the distal end of the second catheter and the first wire. According to some embodiments, such the mechanism as shown in FIG. 3A allows a continuous translation of the second catheter (30) and an adjustable distance between the two treatment locations (4, 6). Similar to what is described in connection with FIG. 2, a second wire 40 can be advanced distally across the mitral annulus (2).

In some embodiments, during the delivery of the second catheter (30), a delivery sheath (8) is used, as seen in FIG. 3A. In one embodiment, the delivery sheath (8) has a single lumen where encloses the first wire (20), the tracking member (52), the second catheter (30), and the tether (50).

Figure 3B:
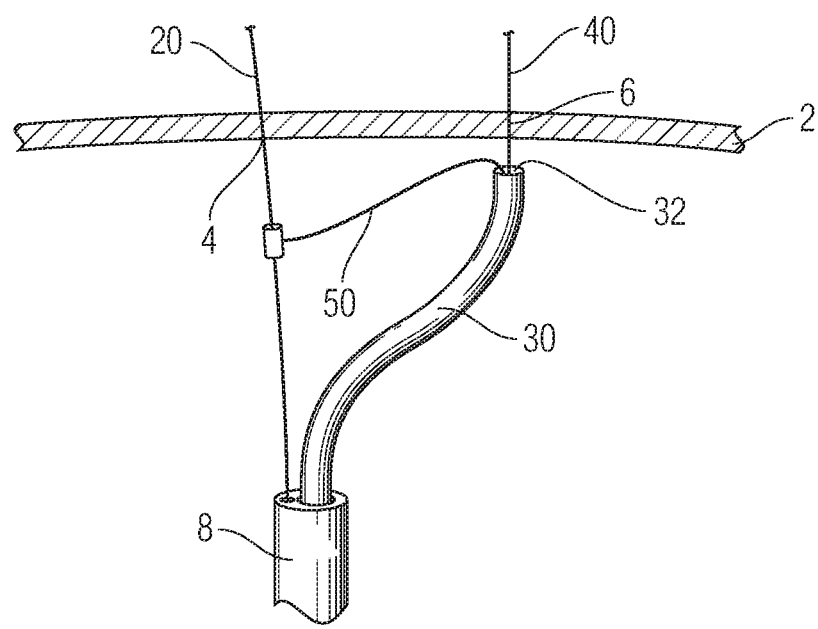
Figure 3C:
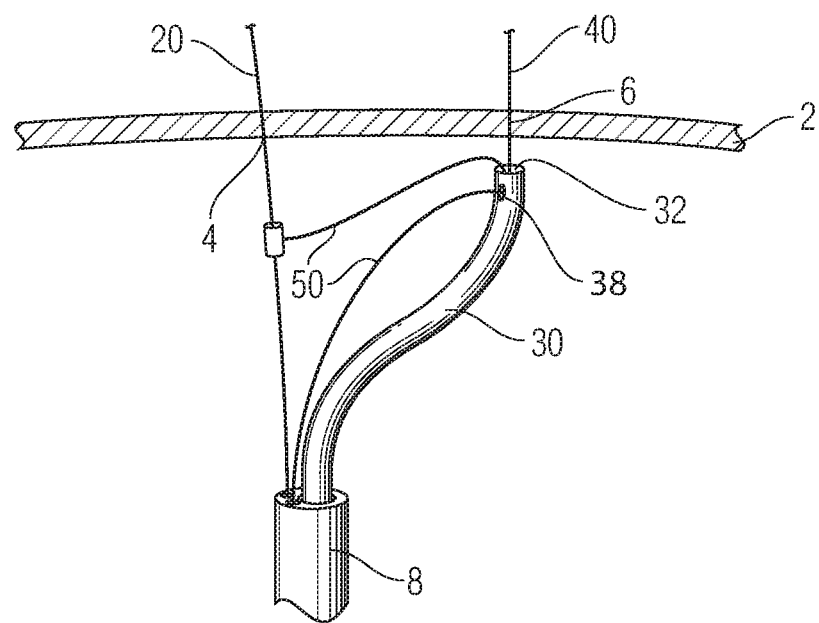

In one embodiment, the tether (50) extends from the tracking element (52), enters the side opening (38) of the second catheter (30), extends proximally along the center lumen (32) of the second catheter (30), and exits the body, as illustrated in FIG. 3A. In another embodiment, the tether (50) extends from the tracking element (52), enters the distal end (34) of the second catheter (30), extends proximally along the center lumen (32) of the second catheter (30), and exits the body, as illustrated in FIG. 3B. In yet another embodiment, the tether (50) extends from the tracking element (52), enters the distal end (34) of the second catheter (30), extends proximally along the center lumen (32) of the second catheter (30), exits a side opening (38) of the second catheter (30), and further extends proximally along the exterior of the second catheter (30), as illustrated in FIG. 3C.

Figure 3D:
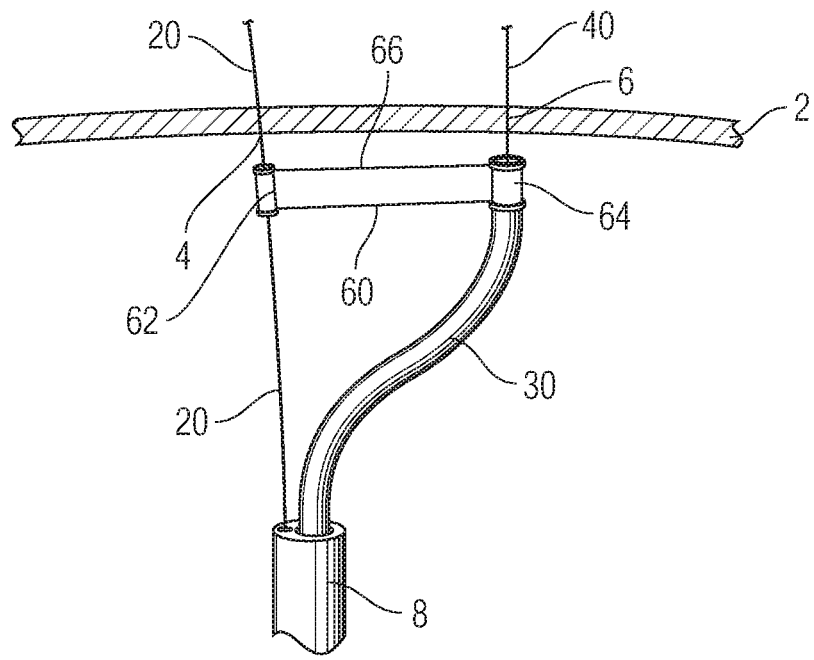

In one embodiment, the first wire delivery catheter (10) and the second wire delivery catheter (30) are different, where the first catheter (10) does not have any attachment mechanism with a tether (50) but the second catheter (30) has. In another embodiment, the first wire delivery catheter (10) and the second wire delivery catheter (30) are the same. In the later embodiment, an attachable/detachable tracking system (60) is used for converting the first catheter to a tethered second catheter. As illustrated in FIG. 3D, the attachable/detachable tracking system (60) includes two tracking anchors (62, 64). The tracking anchors (62, 64) have axial lumens for sliding over the first wire (20) and guiding the second wire (40), respectively. In one embodiment, when the tracking anchor (64) joins the distal end (34) of the second catheter (30), the lumen of the tracking anchor (64) and the lumen (32) of the second catheter (30) forms a continuous conduit for passing the second wire (40).

In one embodiment, as shown in FIG. 3D, at least one tether (66) joins the two tracking anchors (62, 64). In one embodiment, the tether (66) joining two tracking anchors (62, 64) has a fixed length with one end of the tether (66) fixed to one tracking anchor (62) and the other end of the tether (66) fixed to another tracking anchor (64). Thus, the translation distance of the second catheter (30) is predetermined by the length of the tether (66) and so is the distance between the two treatment locations (4, 6).

In another embodiment, one end of the tether (66) is fixed to one tracking anchor (62), riding over the first wire (20), and the other end of the tether (66) enters the other tracking anchor (64) in a manner similar to those described in connection with FIGS. 3A-3C. Thus, the translation of the second catheter (30) can be continuous and adjustable, similar to those described herein.

In various embodiments, at least one of the second catheter and the tether includes a radio-opaque marker or is made in part or its entirety of a radio-opaque material. By using a visualization technique, including various ultrasound, x-ray, fluoroscopic, or magnetic resonance imaging techniques, a clinician can use the marker to visualize where the first catheter, the second catheter, and/or the tether are located in the anatomy. A clinician can also use the marker to determine the translation distance of the second catheter or the distance between the two treatment locations. In one exemplary embodiment, the tether could have multiple markers which to indicate the translation distance, and allow a clinician to control the distance between the two treatment locations.

Figure 4A:
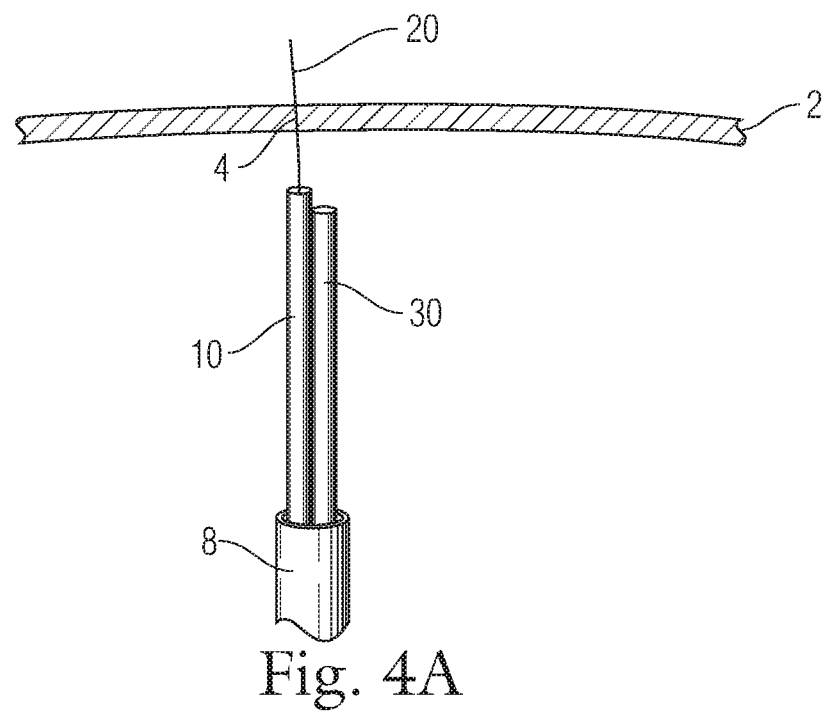
FIGS. 4A-D are perspective views of a translation catheter system in accordance with the present teachings.
Figure 4B:
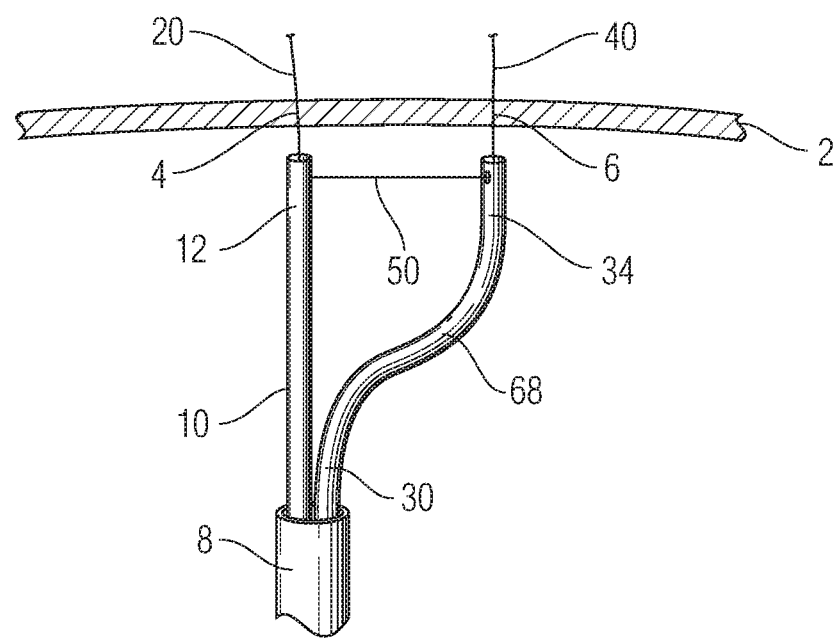
Figure 4C:
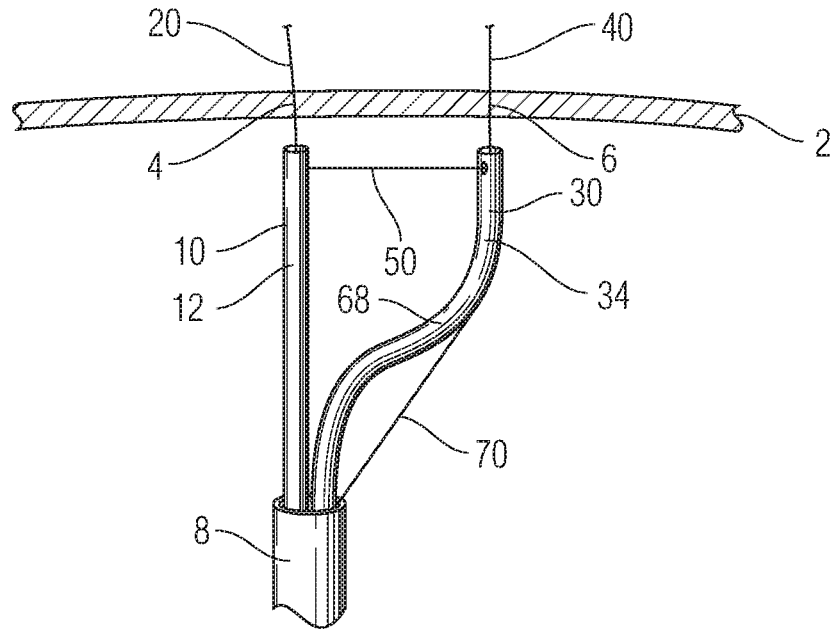

FIGS. 4A-4D illustrate various embodiments of the translatable catheter system according to the present teachings. In some embodiments, as illustrated in FIG. 4B, the first and second catheters (10, 30) are operably joined together at their distal ends (12, 34) by a tether (50) in a manner same as or similar to those described in connection with FIGS. 3A-3C. Optionally, the first and second catheters (10, 30) are operably joined to each other at other places along the catheter bodies.

Referring to FIG. 4A, in some embodiments, the first catheter (10) and the second catheter (30) are delivered together to the mitral annulus (2) while the tether (50) is tightened and the distal ends (12, 34) of the two catheters (10, 30) are held next to each other. In certain embodiments, one of the two catheters (10, 30) is steerable and deflectable, and the steerability and/or deflectability of one of the first and second catheters (10, 30) allows a clinician to advance the distal end (12) of the first catheter (10) to a first location (4) on the annulus (2). In particular embodiments, the second catheter (30) is steerable and deflectable and both the catheters (10, 30) are joined in such way that both the catheters (10, 30) are advanced to the first treatment location (4) by steering the second catheter (30). While the first wire delivery catheter is generally maintained perpendicular to the annulus (2) at the first treatment location (4), a first wire

(20) is advanced across the annulus (2) in a manner similar to those described in connection with FIG. 2.

In various embodiments, a second catheter (30) continuously and adjustably translates away from a first catheter (10) via a tethering mechanism. Now referring to FIG. 4B, while holding the first wire (20) in place, a clinician loosens the tether (50), for example, by extending the tether (50) distally, to allow the distal end (34) of the second catheter (30) to be steered away from the first catheter (10), such as illustrated in FIG. 4B. Without intending to limit the scope of the present teachings, such a lateral movement avoids the distal end of the second catheter from being caught, snag, or hung up by tissues in the left ventricle, and allows the second catheter (30) pushing away any anatomy in the path of the translation. In some embodiments, the distal end (34) of the second catheter (30) remains close to the annulus (2) the entire time when it is steered from the first location to the second location. In some embodiments, the translation of the second catheter (30) from the first location (4) is lateral. In other embodiments, the translation of the second catheter (30) from the first location (4) is continuous. In yet another embodiment, the translation distance of the second catheter (30) from the first location is adjustable.

Similarly, the length of the loosened tether (50) determines the distance between the second catheter (30) and the first catheter (10). According to some embodiments, such the mechanism as shown in FIGS. 4A-4B allows a continuous translation of the second catheter (30) and an adjustable distance between the two treatment locations (4, 6). While the second wire delivery catheter is maintained generally perpendicular to the annulus (2) at its second treatment location (6), a second tissue piercing wire (40) is advanced across the annulus (2) in a manner similar to those described in connection with FIG. 2.

In some embodiments, in order to maintain a generally perpendicular position between the distal end (34) of the second catheter (30) and the annulus (2), the second catheter (30) includes a curved portion (68) near its distal end, as shown in FIG. 4B. In one embodiment, such a curved portion (68) is pre-formed and elastically recoverable to this pre-formed curve when the curved portion (68) of the second catheter (30) is free from the constraint of the tether (50) and/or sheath (8). In another embodiment, such a curved portion (68) is actuated by a mechanical means, for example, by shortening another tether (70) fixed to a portion of the second catheter (30), illustrated in FIG. 4C. One ordinarily skilled in the art would appreciate that other means can also be incorporated to achieve such a configuration. Thus, the specific embodiments disclosed herein should not be construed as limiting.

Figure 4D:
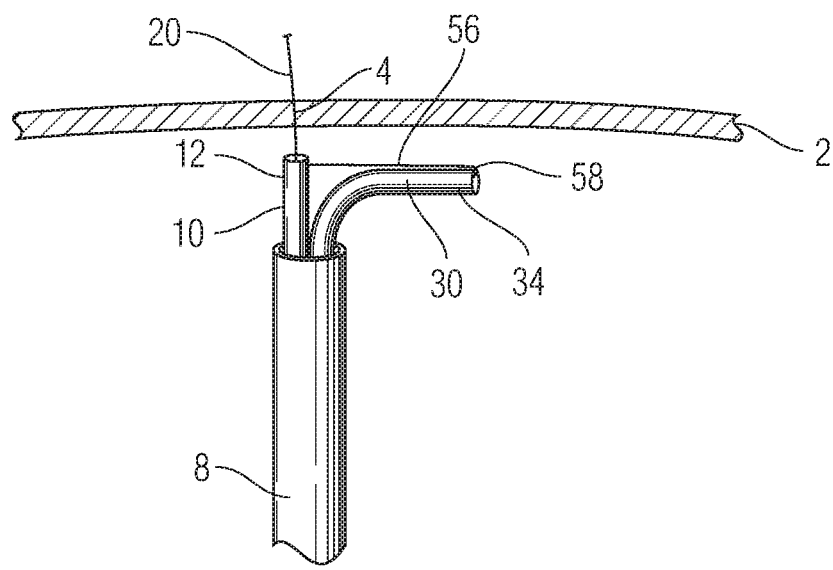

FIG. 4D illustrates another embodiment of the translatable catheter system where the second catheter (30) is configured to roll along the bottom surface of the mitral annulus (2). In such an embodiment, a distal end (58) of the tether (56) fixes to the distal end (34) of the second catheter (30) and the other end of the tether (56) enters the distal end (12) of the first catheter (10), travels proximally along the lumen (not shown) of the first catheter (10), and exits from the body. In some embodiments, the tether (56) is configured in such a way that when it is pushed by a clinician at its proximal end, the distal end (58) of the tether (56) extends laterally away from the first treatment location (4), carrying the distal end (34) of the second catheter (30) with it, as illustrated in FIG. 4D. In some embodiments, a sheath (8) is used to constrain the translation profile of the second catheter (30), as shown in FIG. 4D, so that the distal end (34) of the second catheter (30) and the portions of the second catheter (30) outside of the sheath (8) travels along the bottom surface of the annulus (2) and substantially free from tissues under the annulus, as shown in FIG. 4D. Without intending to limit the scope of the present teachings, such a lateral rolling movement of the distal portion of the second catheter (30) avoids the second catheter from being caught, snag, or hung up by tissues in the left ventricle. In some embodiments, the translation of the second catheter (30) from the first location (4) is lateral. In other embodiments, the translation of the second catheter (30) from the first location (4) is continuous. In yet another embodiment, the translation distance of the second catheter (30) from the first location is adjustable. In other embodiments, the second catheter (30) is made of a flexible tubing so that it can bend and deflect easily without restraint. In some embodiments, after the distal end (34) of the second catheter (30) reaches the second treatment location (6), the sheath (8) is retracted proximally to allow the second catheter (30) to form a more gentle bend, similar to the curve portion (68), as illustrated in FIG. 4B, thereby allowing the second wire (40) to pierce and cross the annulus. According to some embodiment, as the distal portion of the second catheter (30) assumes the more gentle end, the second catheter (30) pushes away any anatomy in the path of the translation.

According to some embodiments, a piece of rigid material could be incorporated to the distal portion of the tether (50) in between of the two catheters (10,30) to ensure a minimal translation distance. In one embodiment, either one of the catheters (10,30) is configured to be articulated. In another embodiment, both of the catheters (10,30) are configured to be articulated.

In many embodiments, the design, material, and/or construct of the first catheter and the second catheter are interchangeable. Specifically, for example, in many of the embodiments described herein, the first catheter maintains its substantially straight configuration while the second catheter is steered away towards the second treatment location. One of ordinary skill in the art would understand that it is equally feasible to have a translatable deliver catheter system where the second catheter maintain its straight profile while the first catheter is steered to push the second catheter to the second treatment site. Thus, parts or portions in connection with the first and second catheters are interchangeable without departing from the letter or the spirit of the present teachings. In various embodiments, at least one of the first catheter, the second catheter, and the tether includes a radio-opaque marker or is made in part or its entirety of a radio-opaque material. By using a visualization technique, including various ultrasound, x-ray, fluoroscopic, or magnetic resonance imaging techniques, a clinician can use the marker to visualize where the first catheter, the second catheter, and/or the tether are located in the anatomy. A clinician can also use the marker to determine the translation distance of the second catheter or the distance between the two treatment locations. In one exemplary embodiment, the tether could have multiple markers which to indicate the translation distance, and allow a clinician to control the distance between the two treatment locations.

Figure 5A:
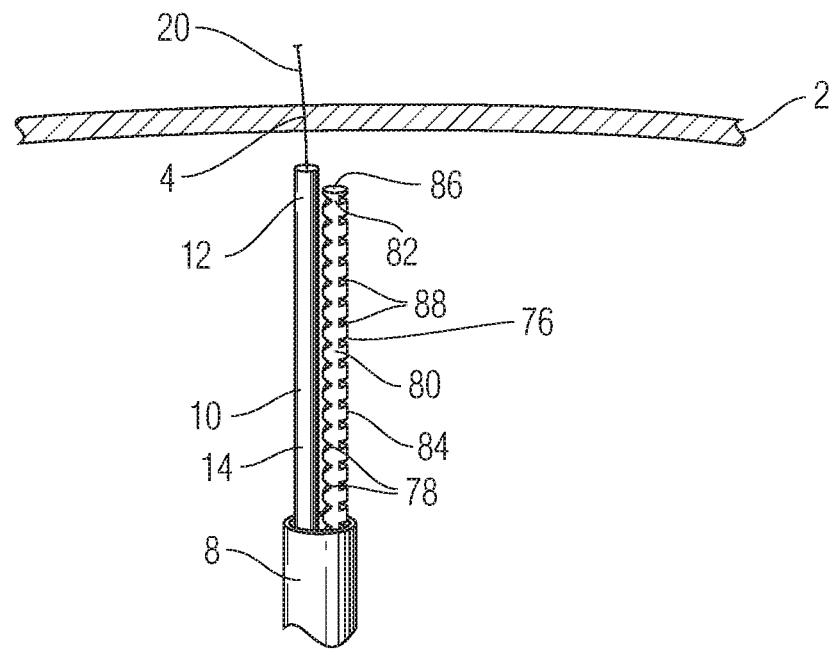
FIGS. 5A-5B are perspective views of a translation catheter system in accordance with the present teachings.
Figure 5B:
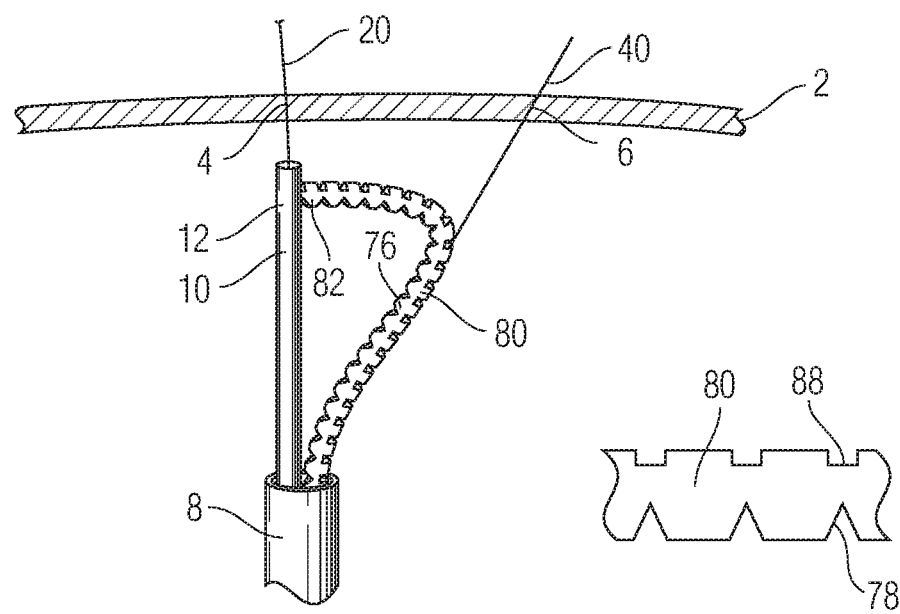
Figure 5C:
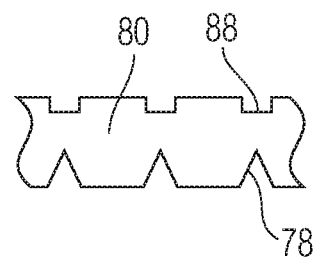
FIG. 5C is a close-up side elevation view of a portion of a catheter showing side openings.

FIGS. 5A-5B illustrates another embodiment of the translatable catheter system according to the present teachings. In the embodiment illustrated in FIG. 5B, the first and second catheters (10, 80) are joined together at their distal ends (12, 82), for example mechanically, thermally, or chemically. The first wire delivery catheter (10) has a configuration same as or similar to those described here. The second wire delivery catheter (80) includes a proximal end (not shown), a distal end (82), and an elongated body (84) with a central lumen (86) therein, where the elongated body extends from the proximal end to the distal end. In some embodiments, the second catheter (80) include a plurality of first side openings (78) located along the longitudinal surface of the catheter and generally facing the first catheter (10) and a plurality of second side openings (88) along the longitudinal surface of the catheter generally across the longitudinal axis of the second catheter (80) from the first side openings (78), as shown in FIGS. 5A-5B. In some embodiments, such a configuration (i.e., having the plurality of first and second side openings (78, 88)) results in a bendable second catheter (80), as shown in FIG. 5B. An embodiment of the second catheter, including openings 78 and 88, is illustrated in FIG. 5C. One ordinarily skilled in the art would understand that other designs can also be used to create such a "hinge" effect, thus the disclosure herein should not be construed as limiting.

As shown in FIG. 5A, a first catheter (10) and a second catheter (80) are delivered together with their distal ends (12, 82) attached to each other and their elongated body (14, 84) side-by-side through the longitudinal lumen of the delivery sheath (8) to a location near the mitral annulus (2). In certain embodiments, one of the two catheters (10, 80) is steerable and deflectable, and the steerability and/or deflectability of one of the first and second catheters (10, 80) allows a clinician to advance the distal end (12) of the first catheter (10) to a first location (4) on the annulus (2). In some embodiments, the translation of the second catheter (80) from the first location (4) is lateral. In other embodiments, the translation of the second catheter (80) from the first location (4) is continuous. In yet another embodiment, the translation distance of the second catheter (80) from the first location is adjustable. In some embodiments, the first catheter (10) is steerable and/or deflectable, so that a clinician can accurately and easily manipulate the distal end (12) of the first catheter (10) to a first location (4) on the annulus (2). A first wire (20) is advanced distally across the annulus (2), similar to what is described in connection with FIG. 2.

FIG. 5B illustrates an exemplary translation of the second catheter (80) according to the present teachings. While maintaining the first wire (20) and the first catheter (10) in place, a clinician extends the second catheter (80) distally. Because the distal end (82) of the second catheter (80) is attached to the distal end (12) of the first catheter (10) and because of the cutting pattern along the elongated body (84) of the second catheter (80), the distal portion (76) of the second catheter (80) rolls laterally outward along the bottom surface of the annulus (2) as shown in FIG. 5B. Without intending to limit the scope of the present teachings, such a lateral rolling/bending movement of the distal portion of the second catheter (80) avoids the second catheter from being caught, snag, or hung up by tissues in the left ventricle. In addition, according to some embodiment, as the distal portion of the second catheter (80) translates to the second treatment location, the second catheter (80) pushes away any anatomy in the path of the translation. The multiple side openings (88) form openings for the second wire (40). A second wire (40) is advanced distally along the lumen (86) of the second catheter (80), exits a side opening (88) of the second catheter (80), and pierces and crosses the mitral annulus (2) at the second treatment location (6). Similarly, one or both of the first catheter (10) and second catheter (80) can include a radio-opaque marker or be made in part or its entirety of a radio-opaque material. In some embodiments, the distal portion (76) of the second catheter (80) has multiple radio-opaque markers to indicate the translation distance and allow a clinician to control the distance between the two treatment locations.

According to another embodiment, instead of extending a second wire (40) directly inside the second catheter (80), a third wire delivery catheter is used to ride inside the lumen of the second catheter (80).

Figure 6A:
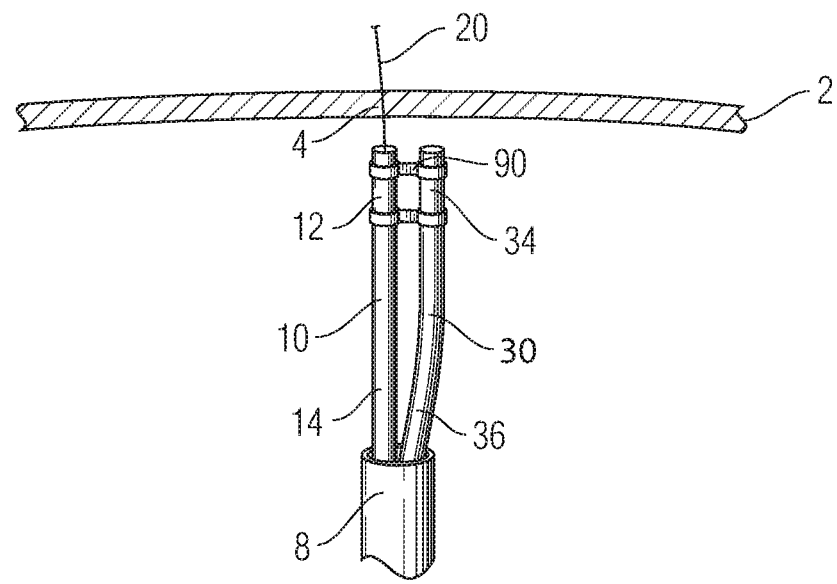
FIGS. 6A-6B are perspective views of a translation catheter system in accordance with the present teachings.
Figure 6B:
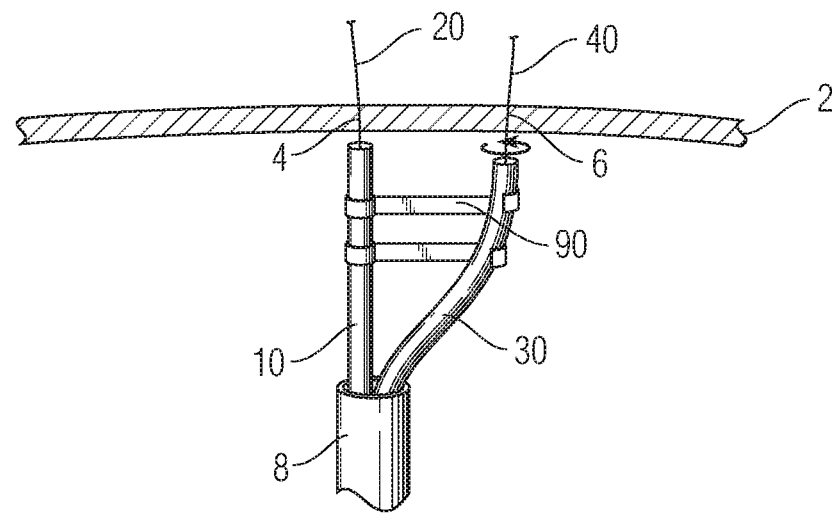

FIGS. 6A-6B illustrate additional exemplary translatable catheter system according to the present teachings. In various embodiments, the first and second catheters (10, 30) are joined together by at least one flexible hinge (90). In some embodiments, one end of the hinge (90) is fixed to one catheter, for example, the first catheter (10), and the other end of the hinge (90) wraps around the distal end of the other catheter, for example, the second catheter (30). In some embodiments, the hinge has a first profile where the hinge winds tightly and holds the first and second catheters (10, 30) side-by-side. In some embodiments, the hinge has a second profile where the hinge (90) loosens and allows the second catheter to translate outward laterally.

In some embodiments, the hinge (90) is in the shape of a coil, a roll, a reel, a spool or alike. In some embodiments, the hinge (90) is closed, open, or relatively neutral at its normal state. In other embodiments, by torquing the distal end of one catheter, the hinge changes from one profile to another. In some embodiments, the hinge (90) has a contoured cross section such that it lies flat against the longitudinal surface of the catheters when wrapped around the distal end portions of the first and second catheters (10, 30). In other embodiments, when the cross section of the hinge straightens, the hinge becomes somewhat rigid, similar to the behavior of a stainless steel tape measure. In some embodiments, the hinge (90) includes multiple radio-opaque markers so that a clinician can visualize the translation distance and control the distance between the two treatment locations.

Similar to those described herein, FIG. 6A illustrates an embodiment of the present teachings where the first catheter (10) and the second catheter (30) are delivered through the longitudinal lumen of the delivery sheath (8) toward the mitral annulus (2), where the distal ends (12,34) are joined together by a hinge (90) and their elongated bodies (14, 36) are aligned side-by-side. Similarly, the steerability and/or deflectability of one of the first and second catheters (10, 30) allows a clinician to advance the distal end (12) of the first catheter (10) to a first location (4) on the annulus (2). A first wire (20) is then advanced distally across the annulus (2), similar to what is described herein.

FIG. 6B illustrates an exemplary translation of a second catheter according to the present teaching. While holding the first wire (20) in place and the first catheter (10) steady, a clinician torques the second catheter (30) to loosen the hinge (90) and translate the second catheter outward laterally. In some embodiments, this lateral translation motion of the second catheter allows the second catheter (30) to push away or ride over any tissues that might be between the two treatment locations (4, 6). In some embodiments, the translation of the second catheter (30) from the first location (4) is lateral. In other embodiments, the translation of the second catheter (30) from the first location (4) is continuous. In yet another embodiment, the translation distance of the second catheter (30) from the first location is adjustable.

In various embodiments, at least one of the first catheter, the second catheter, and the flexible hinge includes a radio-opaque marker or is made in part or its entirety of a radio-opaque material. By using a visualization technique, including various ultrasound, x-ray, fluoroscopic, or magnetic resonance imaging techniques, a clinician can use the marker to visualize where the first catheter, the second catheter, and/or the hinge are located in the anatomy. A clinician can also use the marker to determine the translation distance of the second catheter or the distance between the two treatment locations. In one exemplary embodiment, the hinge could have multiple markers which to indicate the translation distance, and allow a clinician to control the distance between the two treatment locations.

Figure 7A:
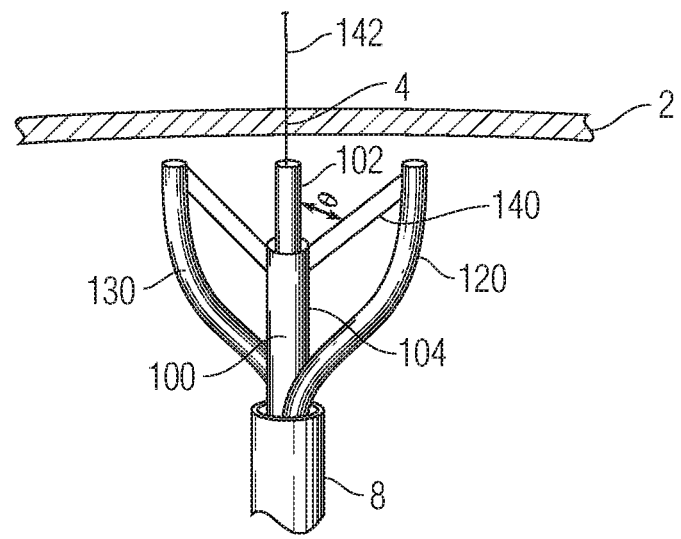
FIGS. 7A-7B are perspective views of a translation catheter system in accordance with the present teachings.
Figure 7B:
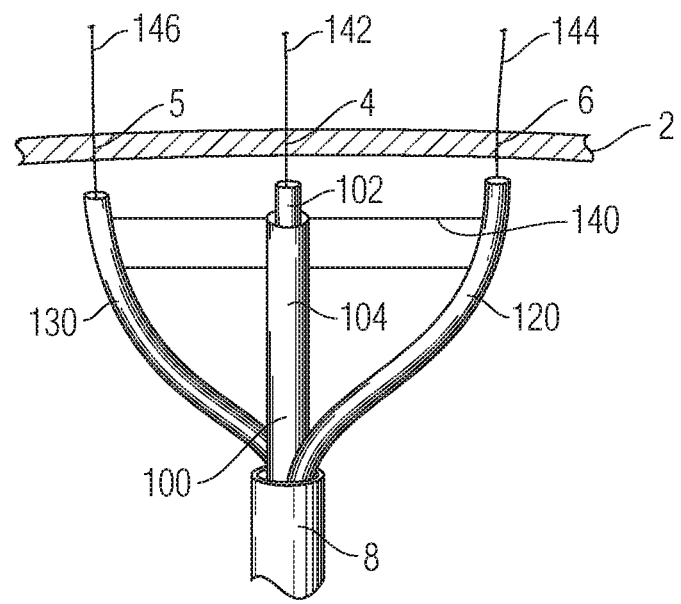

FIGS. 7A-7B illustrate additional exemplary translatable catheter systems. In the embodiments shown in FIGS. 7A-7B, a translatable catheter system includes a trident catheter with a first catheter (100), a second catheter (120), and a third catheter (130). The first catheter (100) includes an inner wire delivery catheter (102) and an outer translation catheter (104). The inner wire delivery catheter (102) is slidably disposed within an axial lumen of the outer translation catheter (104). In this particular embodiment, the inner wire delivery catheter (102) and the outer translation catheter (104) are configured to slide against each other.

In some embodiments, the second catheter (120) is operably joined to the outer translation catheter (104) of the first catheter (100) at their distal end by at least one connecting bar (140). Optionally, a third catheter (130) is operably joined to the outer translation catheter (104) of the first catheter (100) at their distal end by at least one connecting bar (140). In some embodiments, while the inner wire delivery catheter (102) is maintained steady, advancing the outer translation catheter (104) distally causes the connecting bars (140) to push the second and third catheters (120, 130) laterally outward and increase the distance among the distal ends of the catheters, as shown in FIG. 7A. In some embodiments, while the inner wire delivery catheter (102) is maintained steady, retracting the outer translation catheter (104) proximally causes the connecting bars (140) to draw the second and third catheters (120, 130) laterally inward and reduce the distance among the distal ends of the catheters, as shown in FIG. 7A.

Without intending to limit the scope of the present teachings, such a lateral movement of the distal portion of the second and third catheters (120, 130) avoids the second and third catheters (120, 130) from being caught, snag, or hung up by tissues in the left ventricle. In addition, according to some embodiment, as the distal portion of the second and third catheters (120, 130) translates to the second and third treatment location, the second and third catheters (120, 130) pushes away any anatomy in the path of the translation. In some embodiments, the translation of the second and third catheters (120, 130) from the first location (4) is lateral. In other embodiments, the translation of the second and third catheters (120, 130) from the first location (4) is continuous. In yet another embodiment, the translation distance of the second and third catheters (120, 130) from the first location is adjustable.

In some embodiments, the second catheter (120) is at one side of the first catheter (100) and the third catheter (130) is at the other side of the first catheter (100). In some embodiments, the first catheter (100) delivers a first wire (142) across the mitral annulus (2) at a first location (4), the second catheter (120) delivers a second wire (144) across the mitral annulus (2) at a second location (6), and the third catheter (130) delivers a third wire (146) across the mitral annulus (2) at a third location (5). In some embodiments, all three wires (142, 144, 146) are delivered across the annulus (2) simultaneously. In other embodiments, the second and third wires (144, 146) are delivered across the annulus (2) simultaneously. In yet other embodiments, all three wires (142, 144, 146) are delivered across the annulus (2) sequentially. In certain embodiments, the first wire (142) advances across the annulus (2) first, the second wire (144) advances across the annulus (2) second, and the third wire (146) advances across the annulus last.

In some embodiments, the first wire (142) is delivered across the annulus (2) by a single lumen wire delivery catheter (not shown) in a manner similar to those described in connection with FIGS. 1-2. In certain embodiments, when the first wire (142) is advanced across the annulus (2), the single lumen wire delivery catheter (not shown) is retracted proximally and removed from the body. In certain embodiments, the proximal end of the first wire (142) is loaded into the first catheter (100) of the translatable catheter systems, extends from the distal end of the inner wire delivery catheter (102), travels proximally along the axial lumen of the inner wire delivery catheter (102), and exits from the proximal end. Retracting the outer translation catheter (104) proximally to its limits causes the distal ends of the second and third catheters (120, 130) to move close to the distal end of the first catheter (100). This trident translatable catheter system, i.e. all three catheters (100, 120, 130), is advanced distally toward the annulus (2) by tracking the first wire and optionally within a lumen of a delivery sheath (8). In other embodiments, the first wire (142) is placed at the first treatment location (4) on the annulus (2) by the first catheter (100) of the trident catheter system.

FIG. 7A illustrates an exemplary translation of the second and third catheters (120, 130) according to the present teaching. When the distal end of the trident translatable catheter system is located adjacent to the first treatment location (4), the sheath is withdrawn proximally to expose the distal portions of the trident translatable catheter system. While holding the first wire (20) in place and the inner wire delivery catheter (102) steady, a clinician pushes the outer translation catheter (104) distally to cause the connecting bars (140) to expand and push the second and third catheters (120, 130) laterally outward as shown in FIG. 7A. In one embodiment, the further the outer translation catheter (104) is pushed, the further apart the second and third catheters (120, 130) are from the first catheter (100). When the second and third catheters (120, 130) reach the second and third treatment location (5, 6), respectively, the second and third wires (144, 146) are advanced across the annulus (2), as illustrated in FIG. 7B.

In some embodiments, the distal ends of the second and third catheters (120, 130) are always leveled with the distal end of the first catheter (100) during translation. That is, the distal ends of all three catheters are within a same proximity to the mitral annulus (2). Thus, when the second and third catheters (120, 130) translate laterally outward, they push away any tissue in their paths.

According to one embodiment of the present teachings, by visualizing the angle "θ" between the connecting bars (140) and the inner wire delivery catheter (102), as illustrated in FIG. 7A, a clinician can visualize and control the actual translation distance. Similar to various embodiments disclosed in the present teachings, the embodiments described in connection with FIGS. 7A-7B also provide a clinician with a continuous and adjustable catheter translation. Similarly, the lateral translation motions of the second and third catheters allows the catheters (120, 130) to push away or ride over any anatomy that might be between the first treatment location (4) and the second treatment location (6), and the first treatment location (4) and the third treatment location (5). One ordinarily skilled in the art would understand that although a trident catheter system is illustrated and described herein, the same or a similar mechanism can be applied to a bident translatable catheter system, including a dual catheter system. Thus, the specific embodiments described herein should not be construed as limiting.

Figure 8:
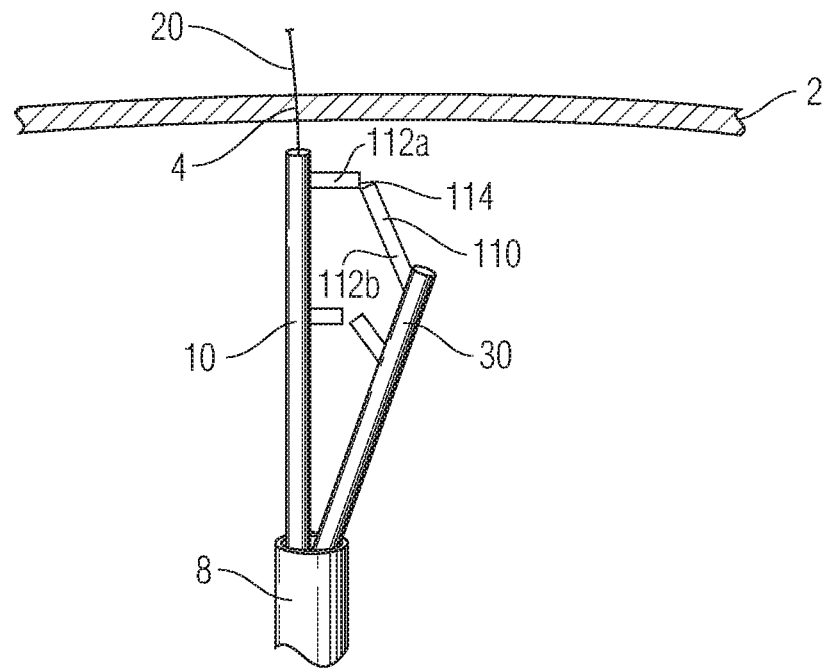
FIG. 8 is a perspective view of a translation catheter system in accordance with the present teachings.

FIG. 8 illustrates another embodiment of the translation catheter system (200) according to the present teachings, where a first and a second catheter are connected by a segmented connecting bar. As seen in FIG. 8, the first catheter (10) connects to the second catheter (30) by at least one connecting bar (110). The at least one connecting bar (110) includes at least two segments (112) and at least one pivot (114).

In some embodiments, the at least one connecting bar (110) is made of a wire and the at least one pivot (114) is made of a single or double coil in the bar. In other embodiments, the at least one pivot (114) is achieved by breaking or disconnecting at least half of the cross section of the connecting bar (110), as shown in FIG. 8. One ordinarily skilled in the art would understand that other methods can also be used to create the at least one pivot on the connecting bar without departing from the letter and spirit of the present teachings. Thus the specific embodiments described herein should not be construed as limiting to the scope of the present teachings.

In some embodiments, as shown in FIG. 8, the at least one pivot (114) on the connecting bar (110) allows the adjacent segments to turn proximally so that the at least one pivot (114) is distal to at least one segment of the connecting bar (110). In other embodiments, the at least one pivot (114) on the connecting bar (110) allows the adjacent segments to turn distally so that the at least one pivot (114) is proximal to at least one segment of the connecting bar (110).

In various embodiments, the segmented connecting bar (110) reduces the space required for the distal-lateral movement of the second catheter (30) during translation, comparing to a non-segmented connecting bar. In other embodiments, the at least one segmented connecting bar (110) each includes two or more segments. In yet other embodiments, the at least one segmented connecting bar (110) each includes three or more segments (112) and two or more pivots (114) between each pair of segments.

FIG. 8 illustrates an exemplary translation of an embodiment of the present teachings. In various embodiments, the translation includes at least one step. In some embodiments, with the first wire (20) in place and the first catheter (10) steady, the second catheter (30) is pushed distally so that the segment (112a) of the connecting bar (110) that is connected with the first catheter swings distally first, as shown in FIG. 8. When the second catheter (30) is pushed further distally, the segment (112b) of the connecting bar (110) that is connected with the second catheter (30) swings distally so that the second catheter (30) reaches the second treatment location. In some embodiments, the translation of the second catheter (30) from the first location (4) is distal-lateral. In other embodiments, the translation of the second catheter (30) from the first location (4) is step-by-step.

Figure 9:
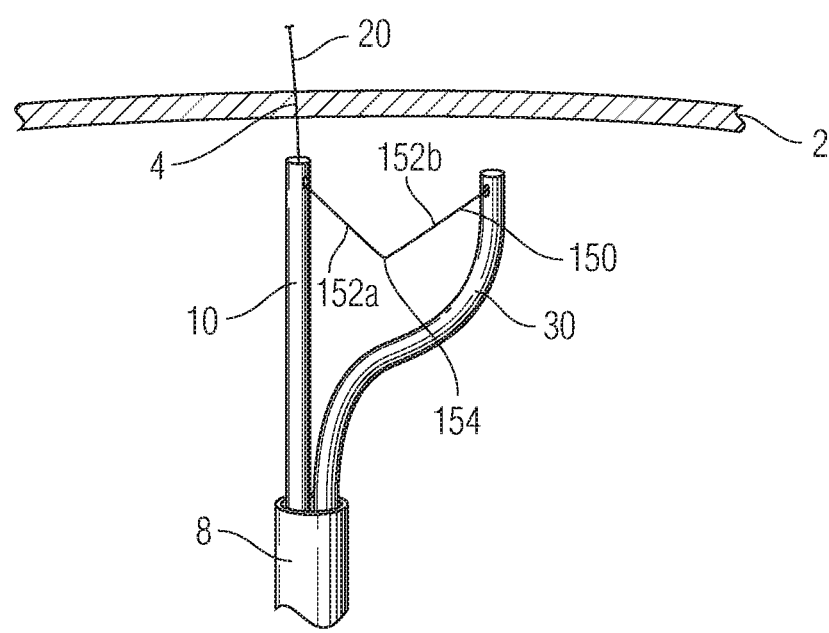
FIG. 9 is a perspective view of a translation catheter system in accordance with the present teachings.

FIG. 9 illustrates another exemplary translation catheter system. In the embodiments shown in FIG. 9, a translatable catheter system includes a bident catheter with a first catheter (10), a second catheter (30) operably connected by a segmented connecting bar (150) at their distal end. Unlike the embodiments described in connection with FIG. 8, the pivot (154) is proximal to all segments (152a, 152b) of the connecting bar (150). In this particular embodiment, the distal ends of the second catheter (30) is always leveled with the distal end of the first catheter (10) during translation, and the distal ends of the first and second catheter (10, 30) are at a substantially same proximity to the annulus.

In some embodiment, after the first wire (20) is put in place and the first catheter (10) is held steady, a clinician steers the distal end of the second catheter (30) laterally away from the distal end of the first catheter (10) causing the connecting bar (150) to unbend. Such a lateral translation of the second catheter (30) pushes away or rides over any tissues in its path and reduces the possibility of the second catheter being caught by the tissues.

According to one embodiment of the present teachings, by visualizing the angle formed between the two segments, a clinician can visualize and control the actual translation distance. Similar to various embodiments disclosed in the present teachings, the embodiments described in connection with FIG. 9 also provide a clinician with a continuous and adjustable catheter translation up to a maximum translation distance. In some embodiments, the translation of the second catheter (30) from the first location (4) is lateral. In other embodiments, the translation of the second catheter (30) from the first location (4) is continuous. In yet another embodiment, the translation distance of the second catheter (30) from the first location is adjustable. One ordinarily skilled in the art would understand that although a bident catheter system is illustrated and described herein, the same or a similar mechanism can be applied to a trident translatable catheter system. Thus, the specific embodiments described herein should not be construed as limiting. The second catheter (30) delivers a second wire (40) across the mitral annulus (2) at a second location (6). In other embodiments, the first and second wires (20, 40) are delivered across the annulus (2) simultaneously. In yet other embodiments, the first and second wires (20, 40) are delivered across the annulus (2) sequentially.

Figure 10A:
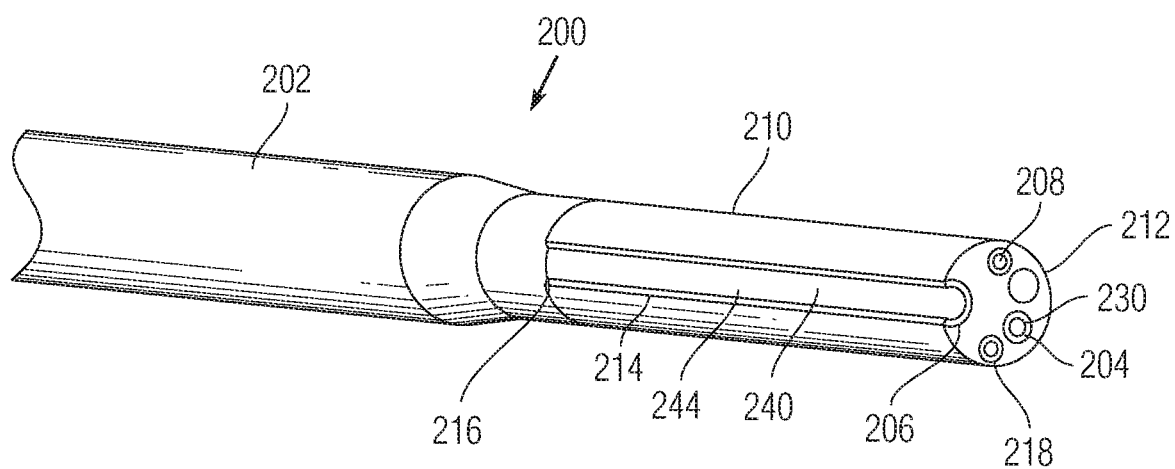
FIG. 10A is a perspective view of a distal end of a translation catheter system in accordance with the present teachings.

FIGS. 10A-10D illustrates another embodiment of the present teaching where a bi-lumen translation catheter system (200) is also configured to be steerable. According to some embodiments, the steerable bi-lumen translation catheter system (200) includes a steerable sheath body (202) with a distal portion (210) and a proximal end (not shown). The steerable sheath body (202) has two wire delivery catheter lumens (204, 206) extends from its proximal end (not shown) to its distal end (212) of the steerable sheath body (202). FIG. 10A illustrates a distal portion (210) of the steerable sheath body (202) having a side slot (214) extending longitudinally from one position (216) of the sheath body (202) all the way to its distal end (212). The slot (214) also extends radially from the second wire delivery lumen (206) all the way to the outer tubular surface of the steerable sheath body (202). The slot (214) is sized and configured to allow a second wire delivery catheter (240) to pivot radially outward to the outside of the steerable sheath body (202). According to some embodiments, the two wire delivery lumens (204, 206) are symmetrical to each other on each side of the longitudinal axis of the steerable sheath body (202). In another embodiment, the two wire delivery lumens (204, 206) can be arranged any other ways suitable for the function of the system.

According to some embodiments of the present teaching, the steerable sheath body (202) is configured to be steerable. As illustrated in FIG. 10A, the steerable sheath body (202) also has two steering wire lumens (208, 218) configured to housing two steering wires (216, 220). Similar to wire delivery catheter lumens (204, 206), the steerable wire lumens (208, 218) also extend from the proximal end of the steerable sheath body (202) longitudinally to the distal end (212). In some embodiments, the two steerable wire lumens (208, 218) are arranged symmetrically on each side of the longitudinal axis of the steerable sheath body (202). One skilled in the art should understand that the two steerable wire lumens (208, 218) can be arranged in other ways suitable for the purpose of the design.

Figure 10B:
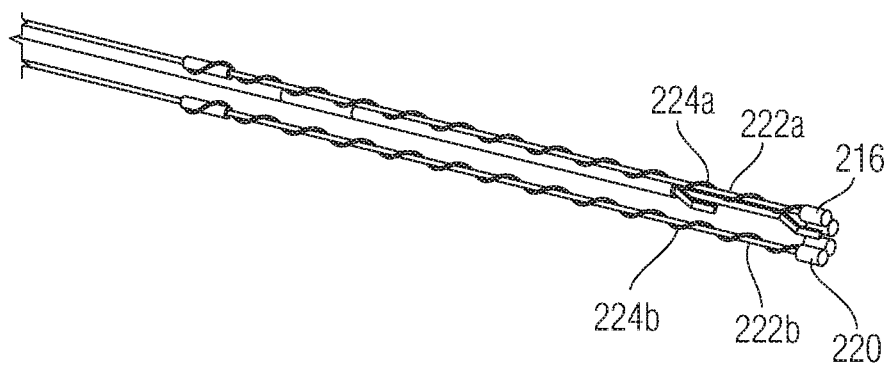
FIG. 10B is a perspective view of a pair of steerable wires for use in the translation catheter system.

FIG. 10B illustrates an exposed view of the steerable wires (216, 220) of the steerable bi-lumen translation catheter system (200). According to one embodiment, each of the steerable wires (216, 220) has a construct of a single longitudinal wire (222a, 222b) with a wire coil (224a, 224b) wrapping around. The distal ends of the wire coil (224a, 224b) and the single longitudinal wire (222a, 222b) are fixed together, and they are also fixed to the distal end (212) of the steerable sheath body (202). The proximal end of the wire coil (224a, 224b) is fixed to the control handle, and the proximal end of the single longitudinal wire (222a, 222b) is configured to be retracted inside the helix of the wire coil (224a, 224b).

According to one embodiment, as the proximal end of a first longitudinal wire (222a) is retracted, the first wire coil (224a) is shortened, and distal portion (210) of the steerable sheath body (202) is steered toward the direction where the first steering wire (216) resides. In another embodiment, as the proximal end of a second longitudinal wire (222b) is retracted, the second wire coil (224b) is shortened, and distal portion (210) of the steerable sheath body (202) is steered toward the direction where the second steering wire (220) resides. Thus, by manipulating either the first or the second longitudinal wires (216, 220), the distal end (212) of the steerable sheath body (202) can be steered to the direction as desired.

According to some embodiments, the steerable bi-lumen translation catheter system (200) further includes two wire delivery catheters (230, 240) as illustrated in FIG. 10A. The first wire delivery catheter (230) is configured to be slidably disposed within the first longitudinal wire delivery catheter lumen (204). The second delivery catheter (240) is configured to be slidably disposed within the second longitudinal wire delivery catheter lumen (206). According to some embodiments, each of the wire delivery catheters (230, 240) also has a tubular body extending from its proximal end to its distal end. The longitudinal lumens of the wire delivery catheters are configured to house a tissue piercing wires similar to what has been described above.

According to some embodiments, the second wire delivery catheter (240) is configured to translate laterally to a first distance from sheath body (202). As described above, the second wire delivery catheter (240) is slidably disposed within the second longitudinal wire delivery catheter lumen (206). The distal portion (244) of the second wire delivery catheter (240) resides within the slot (214) at the distal portion (210) of the steerable sheath body (202) as shown in FIG. 10A.

Figure 10C:
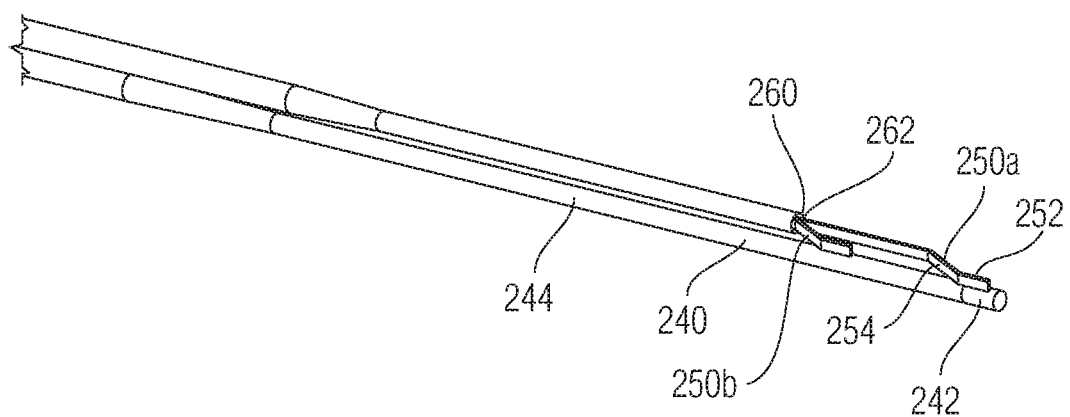
FIG. 10C is a perspective view showing a translation rod assembly for use in the translation catheter system.

FIG. 10C illustrates an exposed view of the distal portion (244) of the second wire delivery catheter (240) and its translation mechanism. In some embodiments, the distal end (242) of the second wire delivery catheter (240) connects to a translation rod (250). FIG. 10C illustrates two translation rods (250a, 250b) that are connected to the distal end portion of the second wire delivery catheter (240) at two locations. One skilled in the art should understand, one translation rod, or more than two translation rods could be used for the purpose. Thus the exemplary embodiments shown here should not be viewed as limiting.

FIG. 10C further illustrates a translation rod lumen (260) extending from the distal portion (210) of the steerable sheath body (202) to its proximal end. The translation rod (250) is configured to be slidably disposed within the translation rod lumen (260). The proximal end of the translation rod (250) connects to the handle and being manipulated by a clinician outside of the body. As illustrated in FIG. 10C, the distal end (262) of the translation rod lumen (260) stop proximal to the distal end (252) of the shortest translation rod (250), and therefore not necessarily at the distal end (212) of the steerable sheath body (202).

Figure 10D:
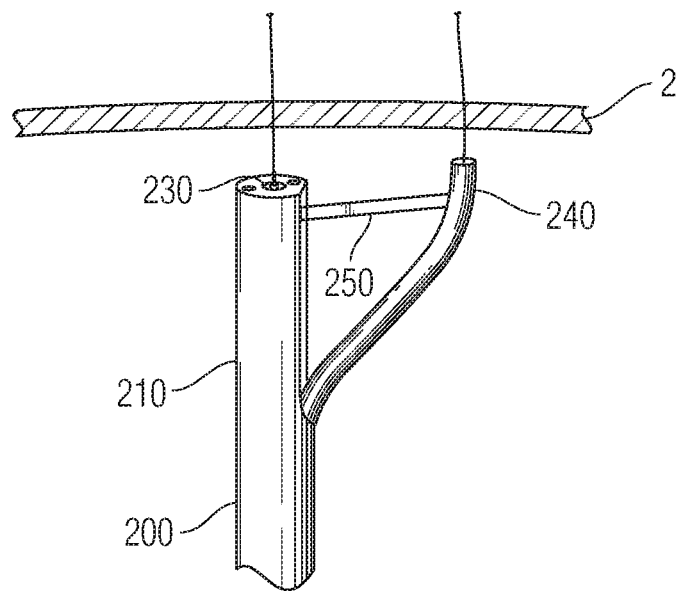
FIG. 10D is a perspective view of a distal end of a translation catheter system.

According to some embodiments of the present teaching, a clinician pushes the proximal end of the translation rod (250), the distal end (252) of the translation rod (250) then pushes on the distal end (242) of the second wire delivery catheter (240). The distal portion (244) of the second wire delivery catheter (240) is then pushed outside of the slot (214) of the steerable sheath body (202), and continue moving laterally to a first distance as illustrated in FIG. 10D According to some embodiments, the translation distance is controlled by the amount of the translation rod (250) pushed by the clinician.

According to some embodiment, as illustrated in FIG. 10C, a distal portion (254) of the translation rod (250) has a pre-bent, which is configured to making sure the translation rod (250) remains a straight line as the distal portion (244) of the second wire delivery catheter (240) moves laterally. In another embodiment, the translation rod (250) is a flat wire band as illustrated in FIG. 10C, which also is configured to ensure that the translation rod (250) remains a straight line as the distal portion (244) of the second wire delivery catheter (240) moves laterally. One skilled in the art should understand that the translation rod could have other profile, such as stepped or smooth exterior, polygon and/or round cross section etc. Thus, the exemplary embodiment in FIG. 10C should not be viewed as limiting.

In some embodiments, the distal end (252) of the translation rod (250) connects to the distal end (242) of the second wire delivery catheter (240). In another embodiment, the distal end (252) of the translation rod (250) connects to a location along the distal portion (244) of the second wire delivery catheter (240). In some embodiment, the translation rod has a cross section size of 2-25 mm, and made of nitinol. Alternatively, the translation rod could be made of any suitable material known to those skilled in the art.

According to some embodiments, the steerable bi-lumen translation catheter system (200) with the second wire delivery catheter (240) collapsed inside the slot (214) of the steerable sheath body (202) is delivered together to the mitral annulus (2). When needed, the distal end of the steerable bi-lumen translation catheter system (200) is steered to the desired location by a clinician pulling on one or both of the steering wires (216, 220). While the first wire delivery catheter (230) is generally maintained perpendicular to the annulus (2) at the first treatment location (4), a first wire is advanced across the annulus (2) in a manner similar to those described in connection with FIG. 2.

In various embodiments, a second wire delivery catheter (240) continuously and adjustably translates away from a wire delivery catheter (230) and the distal portion (210) of the steerable bi-lumen translation catheter system (200) by pushing the translation rod (250) by a clinician. While holding the first wire in place, a clinician pushes the translation rod (250) to allow the distal end (242) of the second wire delivery catheter (240) to be steered away laterally outside of the slot (214) of the steerable bi-lumen translation catheter system (200). Similar to what has been described above, without intending to limit the scope of the present teachings, such a lateral movement avoids the distal end (242) of the second wire delivery catheter (240) from being caught, snag, or hung up by tissues in the left ventricle, and allows the second wire delivery catheter (240) pushing away any anatomy in the path of the translation.

Similarly, the length of the translation rod (250) determines the distance between the second wire delivery catheter (240) and the first wire delivery catheter (230). According to some embodiments, while the second wire delivery catheter (240) is maintained generally perpendicular to the annulus (2) at its second treatment location, a second tissue piercing wire is advanced across the annulus (2) in a manner similar to those described in connection with FIG. 2. FIG. 10D illustrates two wires piercing through the annulus (2). According to some embodiments, the tissue piercing wires are extended inside the wire delivery lumen to and cross annulus after the wire delivery catheter positioned at treatment location. According to some embodiments, the tissue piercing wires are preload inside the wire delivery lumen, and together the wire delivery catheter holding the tissue piercing wires inside are then positioned at treatment location. In some embodiments, when multiple wire delivery catheters presents at treatment location, the multiple tissue piercing wires extends and crosses the annulus simultaneously. In other embodiments, when multiple wire delivery catheters presents at treatment location, the multiple tissue piercing wires extends and crosses the annulus sequentially.

The translation catheter system (200) disclosed above are useful for delivering multiple wires across mitral annulus. One skilled in the art will further recognize that the translation catheter system (200) according to the present teachings could be used to deliver multiple wires across tricuspid annulus, or other heart tissue. In addition, the translation catheter system (200) according to the present teachings could be used to deliver tissue anchors, or other medical implants across a heart tissue.

Various embodiments have been illustrated and described herein by way of examples, and one of ordinary skill in the art will appreciate that variations can be made without departing from the spirit and scope of the present teachings. The present teachings are capable of other embodiments or of being practiced or carried out in various other ways, for example in combinations. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. A method, comprising:
    introducing, into a body of a subject, a catheter system that includes:
        a wire,
        a translatable catheter, having a preformed curved portion proximate a distal end of the translatable catheter,
        a first tether, coupled to the wire, and passing proximally through the translatable catheter, and
        a second tether, attached to the preformed curved portion;
    positioning the catheter system such that the wire is disposed at a first location in the body; and
    while the wire remains at the first location, translating the translatable catheter away from the wire by manipulating the first tether and the second tether.

2. The method according to claim 1, further comprising piercing tissue at the first location with the wire prior to translating the translatable catheter.

3. The method according to claim 1, wherein the catheter system includes a second catheter, the wire extending through the second catheter, and the first tether being coupled to the wire by being coupled to the second catheter, and wherein positioning the catheter system such that the wire is disposed at the first location comprises positioning the catheter system such that the wire extends out of a distal end of the second catheter to the first location.

4. The method according to claim 3, wherein manipulating the first tether comprises increasing an amount of the first tether that is exposed between the translatable catheter and the second catheter.

5. The method according to claim 3, wherein the catheter system comprises a delivery sheath, and wherein introducing the catheter system into the body comprises introducing the catheter system into the body while the translatable catheter and the second catheter are disposed within the delivery sheath.

6. The method according to claim 5, wherein the delivery sheath is steerable, and wherein introducing the catheter system into the body comprises steering the delivery sheath.

7. The method according to claim 5, wherein:
    the delivery sheath has a tubular outer surface, and defines a first lumen and a second lumen,
    the translatable catheter extends through the first lumen,
    the second catheter extends through the second lumen,
    the delivery sheath defines a side-slot that opens a distal portion of the first lumen laterally through the tubular outer surface, and
    translating the translatable catheter comprises moving the preformed curved portion laterally through the side-slot.

8. The method according to claim 1, wherein the wire is a first wire, and wherein the method further comprises advancing a second wire out of the translatable catheter to a second location.

9. The method according to claim 8, further comprising piercing tissue at the first location with the first wire.

10. The method according to claim 9, further comprising piercing tissue at the second location with the second wire.

11. The method according to claim 10, wherein piercing tissue at the first location with the first wire comprises piercing tissue at the first location with the first wire prior to translating the translatable catheter.

12. The method according to claim 11, wherein piercing tissue at the second location with the second wire comprises piercing tissue at the second location with the second wire subsequently to translating the translatable catheter.

13. The method according to claim 3, wherein manipulating the second tether comprises tensioning the second tether.

14. A method, comprising:
    introducing, into a body of a subject, a catheter system that includes:
        a catheter, having a curveable portion proximate a distal end of the catheter,
        a first tether, coupled to a first portion of the catheter system, and passing proximally through at least a portion of the catheter, and a second tether, attached to the curveable portion;
positioning the catheter system such that the first portion is disposed at a first location in the body;
piercing tissue at the first location with the first portion; and
subsequently to piercing the tissue at the first location, and while the first portion remains at the first location, translating the catheter away from the first portion by manipulating the first tether and the second tether.

15. The method according to claim 14, wherein the catheter system includes a second catheter, the first tether being coupled to the first portion by being coupled to the second catheter, and wherein positioning the catheter system such that the first portion is disposed at the first location comprises positioning the catheter system such that the first portion extends from the second catheter to the first location.

16. The method according to claim 15, wherein manipulating the first tether comprises increasing an amount of the first tether that is exposed between the catheter and the second catheter.

17. The method according to claim 15, wherein the catheter system comprises a delivery sheath, and wherein introducing the catheter system into the body comprises introducing the catheter system into the body while the catheter and the second catheter are disposed within the delivery sheath.

18. The method according to claim 17, wherein:
the delivery sheath has a tubular outer surface, and defines a first lumen and a second lumen,
the catheter extends through the first lumen,
the second catheter extends through the second lumen,
the delivery sheath defines a side-slot that opens a distal portion of the first lumen laterally through the tubular outer surface, and
translating the catheter comprises moving the curveable portion laterally through the side-slot.

19. The method according to claim 14, wherein:
the first portion is a first wire,
piercing tissue at the first location with the first portion comprises piercing tissue at the first location with the first wire, and
the method further comprises advancing a second wire out of the catheter to a second location, and piercing tissue at the second location with the second wire.

20. A method, comprising:
introducing, into a body of a subject, a catheter system that includes:
a first catheter, having a curveable portion proximate a distal end of the first catheter,
a second catheter, and
a first tether, coupled to the second catheter, and passing proximally through at least a portion of the first catheter, and
a second tether, attached to the curveable portion;
positioning the catheter system such that the curveable portion extends from the second catheter to be disposed at a first location in the body; and
while the curveable portion remains at the first location, translating the second catheter away from the curveable portion by manipulating the second tether and manipulating the first tether in a manner that increases an amount of the first tether that is exposed between the first catheter and the second catheter.

21. The method according to claim 20, further comprising, prior to translating the second catheter, securing the curveable portion at the first location by piercing tissue at the first location.

22. The method according to claim 20, wherein the catheter system comprises a delivery sheath, and wherein introducing the catheter system into the body comprises introducing the catheter system into the body while the first catheter and the second catheter are disposed within the delivery sheath.

23. The method according to claim 22, wherein:
the delivery sheath has a tubular outer surface, and defines a first lumen and a second lumen,
the first catheter extends through the first lumen,
the second catheter extends through the second lumen,
the delivery sheath defines a side-slot that opens a distal portion of the first lumen laterally through the tubular outer surface, and
translating the second catheter comprises moving the curveable portion laterally through the side-slot.

24. The method according to claim 21, wherein a first wire is used to pierce the tissue at the first location, and wherein the method further comprises advancing a second wire out of the second catheter to a second location, and piercing tissue at the second location with the second wire.

* * * * *